United States Patent [19]

Martin et al.

[11] Patent Number: 4,707,182
[45] Date of Patent: Nov. 17, 1987

[54] PHENOXINE-KETAL ETHERS, COMPOSITIONS CONTAINING THEM AND THE USE THEREOF

[75] Inventors: Henry Martin, Allschwil; Urs Fricker, Gelterkinden, both of Switzerland

[73] Assignee: Ciba-Geigy Corporation, Ardsley, N.Y.

[21] Appl. No.: 733,353

[22] Filed: May 13, 1985

Related U.S. Application Data

[62] Division of Ser. No. 473,905, Mar. 10, 1983, Pat. No. 4,530,716.

[30] Foreign Application Priority Data

Mar. 15, 1982 [CH] Switzerland ............... 1609/82

[51] Int. Cl.⁴ ............... A01N 43/40; A01N 43/08; C07D 317/16; C07D 319/06
[52] U.S. Cl. ............... 71/94; 549/347; 549/372; 549/373; 71/88; 71/92; 71/93; 71/100; 71/108; 71/111; 71/118; 71/125
[58] Field of Search ............ 549/373, 372, 347; 71/88, 92, 94, 93

[56] References Cited

U.S. PATENT DOCUMENTS 4,269,775  5/1981  Szczepanski et al. ............... 549/373

Primary Examiner—Nicky Chan
Attorney, Agent, or Firm—Edward McC. Roberts

[57] ABSTRACT

The oxime ethers of the formula I below are able to act as antidotes or safeners to protect cultivated plants from the phytotoxic effects of herbicides. Such cultivated plants are preferably sorghum, cereals, maize and rice, and herbicides are principally chloroacetanilides and thiocarbamates. The oxime ethers have the formula I

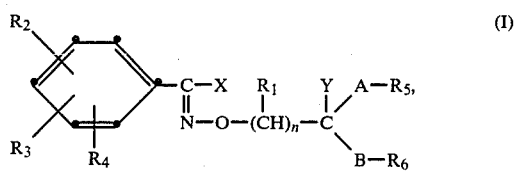

wherein n is 1 or 2, each of $R_1$ and $R_2$ is hydrogen or $C_1$-$C_4$ alkyl each of $R_3$ and $R_4$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ alkylsulfonyl, $C_1$-$C_4$ haloalkylsulfinyl, $C_1$-$C_4$ haloalkylsulfonyl or nitro; each of $R_5$ and $R_6$ independently of the other is $C_1$-$C_4$ alkyl, $C_1$-$C_4$ haloalkyl, $C_2$-$C_8$ alkoxyalkyl, $C_3$-$C_4$ alkenyl, $C_3$-$C_4$ alkynyl, or together form a 2- to 6-membered alkylene or alkenylene bridge which may be substituted by 1 to 4 $C_1$-$C_4$ alkyl, $C_1$-$C_4$ haloalkyl, $C_1$-$C_4$ alkoxy, $C_2$-$C_4$ alkenyloxy, $C_2$-$C_8$ alkoxyalkyl or $C_3$-$C_8$ alkenyloxyalkyl groups; each of A and B independently of the other is oxygen or sulfur, or one of A and B is the methine group, X is a fluorinated $C_1$-$C_3$ alkyl radical which may also additionally contain chlorine, and Y is hydrogen, $C_1$-$C_4$ alkyl, $C_1$-$C_4$ haloalkyl, $C_1$-$C_4$ alkoxy, $C_1$-$C_4$ haloalkoxy or phenyl.

12 Claims, No Drawings

PHENOXINE-KETAL ETHERS, COMPOSITIONS CONTAINING THEM AND THE USE THEREOF

This is a divisional of application Ser. No. 473,905, filed on Mar. 10, 1983, now U.S. Pat. No. 4,530,716, issued July 23, 1985.

The present invention relates to novel oxime ethers, to the preparation thereof, to compositions for protecting cultivated plants from the phytotoxic effects of herbicides, which compositions contain the novel oxime ethers as active component, and to the use thereof.

It is known that herbicides belonging to a very wide range of compound classes such as triazines, urea derivatives, carbamates, thiocarbamates, haloacetanilides, halophenoxyacetic acids etc., when employed in an effective concentration, often also damage cultivated plants to a certain extent in addition to the weeds which it is desired to control. To counteract this problem, different compounds have already been proposed which are able specifically to antagonise the harmful action of the herbicide on the cultivated plant, i.e. to protect the cultivated plant without noticeably influencing the herbicidal action on the weeds to be controlled. However, it has been found that the proposed antidotes very often have a species-specific activity both with respect to the cultivated plants and to the herbicide and also, in some cases, contingent on the mode of application, i.e. a specific antidote is often suitable only for a specific cultivated plant and a few classes of herbicides.

For example, British patent specification No. 1 277 557 describes the protective treatment of seeds or seedlings of wheat and sorghum with certain oxamic acid esters and amides against attack by "ALACHLOR" (N-methoxymethyl-N-chloroacetyl-2,6-diethylaniline). Antidotes for treating cereals, maize and rice seeds against the harmful effects of herbicidal thiocarbamates are proposed in German Offenlegungsschrift specification Nos. 1 952 910 and 2 245 471 and in French patent specification No. 2 021 611. German patent specification No. 1 576 676 and U.S. Pat. No. 3,131,509 disclose the use of hydroxyaminoacetanilides and hydantoins for protecting cereal seeds against the effects of carbamates.

The direct pre- or postemergence treatment of certain useful plants with antidotes as antagonists of specific classes of herbicides in a crop area is disclosed in German Offenlegungsschrift specifications Nos. 2 141 586 and 2 218 097 and in U.S. Pat. No. 3,867,444.

Further, German Offenlegungsschrift No. 2 402 983 discloses that maize plants can be effectively protected against damage by chloroacetanilides by adding an N-substituted dichloroacetamide as antidote to the soil.

According to European patent application No. 11.047, alkoximinobenzylcyanides, in which the alkoxy group is substituted, inter alia, by an acetalised carbonyl group, can be used as antidotes for protecting cultivated plants from the harmful effects of herbicides belonging to different classes of compounds.

The present invention relates to novel oxime ethers of the formula I

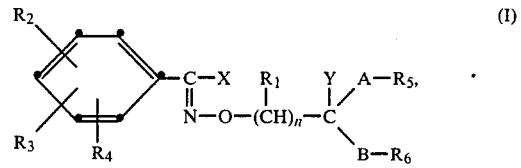

wherein n is 1 or 2, each of $R_1$ and $R_2$ is hydrogen or $C_1$–$C_4$ alkyl each of $R_3$ and $R_4$ is hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_4$ alkylsulfinyl, $C_1$–$C_4$ alkylsulfonyl, $C_1$–$C_4$ haloalkylsulfinyl, $C_1$–$C_4$ haloalkylsulfonyl or nitro; each of $R_5$ and $R_6$ independently of the other is $C_1$–$C_4$ alkyl, $C_1$–$C_4$ haloalkyl, $C_2$–$C_8$ alkoxyalkyl, $C_3$–$C_4$ alkenyl, $C_3$–$C_4$ alkynyl, or together form a 2- to 6-membered alkylene or alkenylene bridge which may be substituted by 1 to 4 $C_1$–$C_4$ alkyl, $C_1$–$C_4$ haloalkyl, $C_1$–$C_4$ alkoxy, $C_2$–$C_4$ alkenyloxy, $C_2$–$C_8$ alkoxyalkyl or $C_3$–$C_8$ alkenyloxyalkyl groups; each of A and B independently of the other is oxygen or sulfur, or one of A and B is the methine group, X is a fluorinated $C_1$–$C_3$ alkyl radical which may also additionally contain chlorine, and Y is hydrogen, $C_1$–$C_4$ alkyl, $C_1$–$C_4$ haloalkyl, $C_1$–$C_4$ alkoxy, $C_1$–$C_4$ haloalkyl or phenyl.

The $C_1$–$C_4$ alkyl groups represented by or contained in the radicals $R_1$ to $R_6$ may be straight chain or branched and are individually methyl, ethyl, n-propyl, isopropyl, n-butyl, sec-butyl, isobutyl and tert-butyl. Among these alkyl groups, $C_1$–$C_2$ alkyl groups are preferred and $R_1$ as alkyl is preferably methyl.

Halogen denotes fluorine, chlorine, bromine and iodine, with fluorine and chlorine being preferred.

The fluorinated alkyl radical X may be e.g. difluoromethyl, trifluoromethyl, chlorodifluoromethyl, tetrafluoroethyl, pentafluoroethyl, difluorochlorofluoroethyl and heptafluoropropyl. Among these radicals X, perfluorinated alkyl radicals are preferred in which one fluorine atom may be replaced by a chlorine atom. Particularly preferred radicals X are trifluoromethyl, chlorodifluoromethyl and pentafluoroethyl.

Depending on the significance of A, B and Y, different ether or thioether derivatives are obtained. Where each of A and B is oxygen, Y is hydrogen and each of $R_5$ and $R_6$ is alkyl, alkenyl or substituted alkyl, acetals are obtained. Where $R_5$ and $R_6$ together form an alkylene or alkenylene bridge, cyclic acetals are obtained, e.g. 1,3-dioxolanes, 1,3-dioxane, 1,3-dioxepane or 1,3-dioxep-5-one derivatives as well as higher dioxo ring systems.

Where each of A and B is sulfur, Y is hydrogen and each of $R_5$ and $R_6$ is a hydrocarbon radical, thioacetals are obtained. Where $R_5$ and $R_6$ together form a hydrocarbon bridge, dithiolones and dithianes are obtained.

Where each of A and B is oxygen and Y is alkyl or phenyl, ketals are obtained. Thioketals are obtained if A and B are sulfur.

Orthoesters are obtained where each of A and B is oxygen, Y is alkoxy and each $R_5$ and $R_6$ is a hydrocarbon radical. Cyclic orthoesters are obtained where $R_5$ and $R_6$ together form a hydrocarbon bridge.

A may also be oxygen, B methylene and Y hydrogen, and $R_5$ and $R_6$ together form a hydrocarbon bridge, to give furane, dihydrofurane, tetrahydrofurane, pyrane, di- or tetrahydropyrane derivatives and similar oxygen ring derivatives.

Different preparatory methods are often employed for these types of compounds.

The following variants of compounds of the formula I are possible:

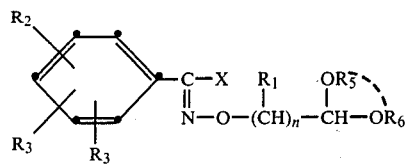

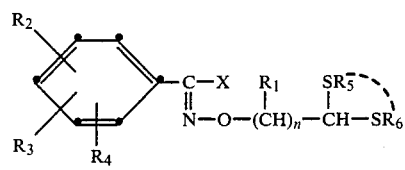

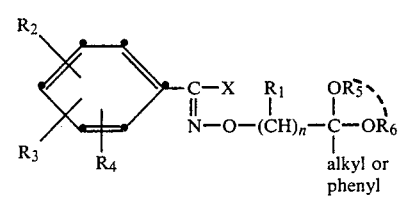
alkyl or phenyl

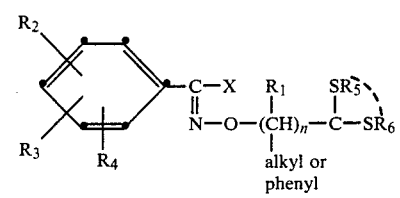
alkyl or phenyl

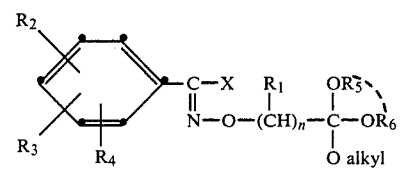
O alkyl

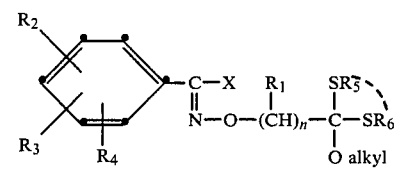
O alkyl

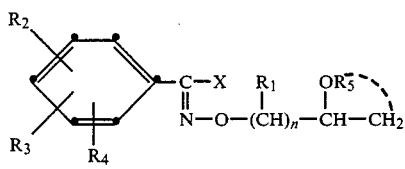

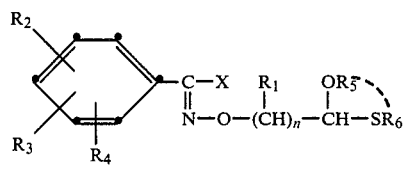

The oxime ethers of the formula I accordingly take the form of the following subgroups, for example as
(a) acetal derivatives of the formula II

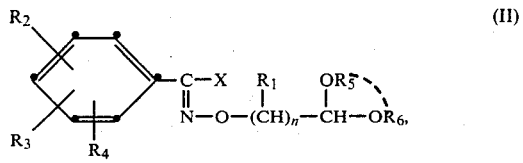

wherein n, $R_1$, $R_2$, $R_3$, $R_4$ and X are as defined for formula I and each of $R_5$ and $R_6$ independently of the other is $C_1-C_4$ haloalkyl, $C_2-C_8$ alkoxyalkyl, $C_3-C_4$ alkenyl or $C_3-C_4$ alkynyl, i.e. they may be the same or different and are e.g. methyl, ethyl, propyl, isopropyl, butyl, chloroethyl, bromoethyl, methoxyethyl, allyl or propargyl;

(b) ortho-esters of the formula III

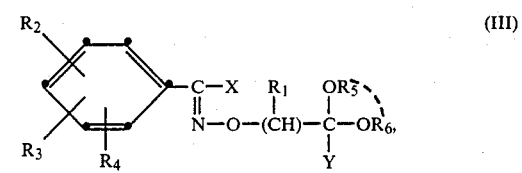

wherein n, $R_1$, $R_2$, $R_3$, $R_4$ and X are as defined for formula I, each of $R_5$ and $R_6$ independently of the other is $C_1-C_4$ alkyl, $C_1-C_4$ haloalkyl, $C_2-C_8$ alkoxyalkyl, $C_3-C_4$ alkenyl or $C_3-C_4$ alkynyl and Y is $C_1-C_4$ alkoxy;

(c) ring derivatives, e.g. the 1,3-dioxane, 4,7-dihydro, 1,3-dioxepine compounds of the formulae IV and IVa

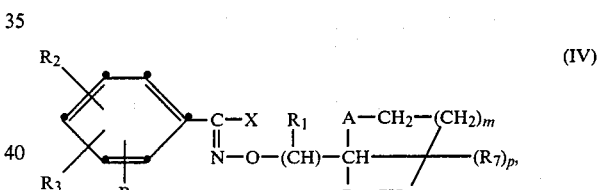

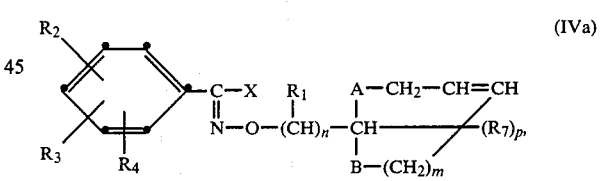

wherein n, $R_1$, $R_2$, $R_3$, $R_4$, A, B and X are as defined for formula I, each of m and p is 0 or 1, 2 or 3, $R_7$ is $C_1-C_4$ alkyl, $C_1-C_4$ haloalkyl, $C_2-C_8$ alkoxyalkyl or alkenyloxyalkyl, preferably methyl. Those ring derivatives are preferred in which A and B are oxygen and have the formula V

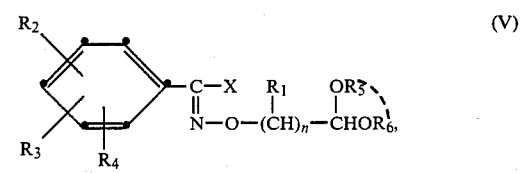

wherein n, $R_1$, $R_2$, $R_3$, $R_4$ and X are as defined for formula I and $R_5$ and $R_6$ together form a 2- to 6-membered alkylene or alkenylene bridge which may be substituted by 1 to 3 $C_1$-$C_4$ alkyl, $C_1$-$C_4$ haloalkyl, $C_2$-$C_8$ alkoxyalkyl or alkenyloxyalkyl groups.

Among these compounds, the following are in turn preferred:

(d) compounds in which n is 1, each of $R_1$, $R_2$, $R_4$ and Y is hydrogen, $R_3$ is in the 4-position and is hydrogen, halogen, methyl, difluoromethyl, trifluoromethyl, chlorodifluoromethyl, methoxy, difluoromethoxy, trifluoromethoxy, chlorodifluoromethoxy, tetrafluoroethyl, tetrafluoroethoxy or trifluoromethylsulfonyl, each of A and B is oxygen, X is trifluoromethyl, chlorodifluoromethyl or pentafluoroethyl, and $R_5$ and $R_6$ are as defined for formula I;

(e) compounds in which n is 1, each of $R_1$, $R_2$, $R_4$ and Y is hydrogen, $R_3$ is in the 4-position and is hydrogen, fluorine, chlorine, methyl, difluoromethyl, trifluoromethyl, chlorodifluoromethyl, methoxy, difluoromethoxy, trifluoromethoxy, chlorodifluoromethoxy, tetrafluoroethyl, tetrafluoroethoxy or trifluoromethylsulfonyl, each of A and B is oxygen, X is trifluoromethyl, chlorodifluoromethyl or pentafluoroethyl, and $R_5$ and $R_6$ together are a 1,2-ethylene, or 1,3-propylene group which is unsubstituted or substituted by 1 to 4 methyl, chloromethyl, $C_1$-$C_4$ alkoxy or $C_2$-$C_4$ alkenyloxy groups;

(f) compounds in which n is 1, $R_1$, $R_2$ and $R_4$ are hydrogen, $R_3$ is in the 4-position and is hydrogen, fluorine, chlorine, methyl, trifluoromethyl or trifluoromethoxy, each of A and B is oxygen, X is trifluoromethyl, chlorodifluoromethyl or pentafluoroethyl, and $R_5$ and $R_6$ together are a 1,2-ethylene group which is unsubstituted or substituted by 1 to 4 methyl groups;

(g) compounds in which n is 1 each of $R_1$, $R_2$, $R_4$ and Y is hydrogen, $R_3$ is in the 2-position and is fluorine or chlorine, each of A and B is oxygen and $R_5$ and $R_6$ together are a 1,2-ethylene or 1,3-propylene group which is unsubstituted or substituted by 1 to 4 methyl groups; and (h) compounds in which n is 1, each of $R_1$, $R_2$, $R_4$ and Y is hydrogen, $R_3$ is in the 3-position and is trifluoromethyl or nitro, each of A and B is oxygen, X is trifluoromethyl, chlorodifluoromethyl or pentafluoromethyl, and $R_5$ and $R_6$ together are a 1,2-ethylene or 1,3-propylene group which is unsubstituted or substituted by 1 to 4 methyl groups.

Preferred individual compounds are:

1-phenyl-1-(1,3-dioxolan-2-ylmethoximino)-2,2,2-trifluoroethane, 1-(4-chlorophenyl)-1-(1,3-dioxolan-2-ylmethoximino)-2,2,2-trifluoroethane, 1-(4-chlorophenyl)-1-(2,2-diethoxyethoximino)-2,2,2-trifluoroethane, 1-(4-chlorophenyl)-1-(2,2-dimethoxyethoximino)-2,2,2-trifluoroethane, 1-(4-fluorophenyl)-1-(1,3-dioxolan-2-ylmethoximino)-2,2,2-trifluoroethane, 1-(3,4-dimethylphenyl-1-(1,3-dioxolan-2-ylmethoximino)-2,2,2-trifluoroethane, 1-(4-fluorophenyl)-1-(1,3-dioxolan-4-methyl-2-ylmethoximino)-2,2,2-trifluoroethane, 1-phenyl-1-(1,3-dioxan-2-ylmethoximino)-2,2,2-trifluoroethane, 1-(3-trifluoromethylnaphthyl)-1-(1,3-dioxan-2-ylmethoximino)-2,2,2-trifluoroethane, 1-phenyl-1-(1,3-dioxolan-2-ylmethoximino)-2,2,3,3,3-pentafluoropropane, 1-(4-chlorophenyl)-1-(1,3-dioxolan-2-ylethoximino)-2,2,2-trifluoroethane, 1-(4-fluorophenyl)-1-(1,3-dioxan-2-ylmethoximino)-2,2,2-trifluoroethane, 1-(4-fluorophenyl)-1-(1,3-dioxolan-2-ylethoximino)-2,2,2-trifluoroethane, 1-(4-chlorophenyl)-1-(1,3-dioxolan-4,5-dimethyl-2-ylmethoximino)-2,2,2-trifluoroethane, 1-(3-trifluoromethylphenyl)-1-(1,3-dioxolan-4-ethyl-2-ylmethoxyimino)-2,2,2-trifluoroethane.

The novel oxime ethers of the formula I are prepared by reacting a salt of an oxime of the formula VI

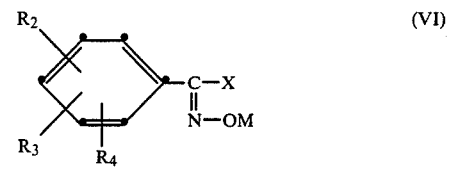

in which M is an alkali metal cation or an alkaline earth metal cation and $R_2$, $R_3$, $R_4$ and X have the above meanings, with a haloalkyl ether of the formula VII

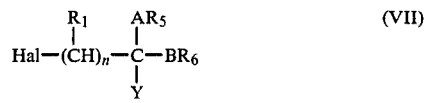

in which Hal is a halogen atom, preferably a chlorine atom or a bromine atom, and A, B, n, $R_1$, $R_5$ and Y are as defined above. Suitable salts of an oxime of the formula VI are in particular the sodium and potassium salts. The reaction of the oxime of formula VI with the haloalkyl ether of formula VII is conveniently carried out in an inert organic solvent. Particularly suitable solvents are polar solvents such as acetonitrile, dimethylformamide and dimethylsulfoxide.

The reactants are normally employed in equimolar amount. However, an excess of one or other reactant may also be employed to bring the reaction to completion. The reaction is conveniently carried out at elevated temperature, preferably in the range from 60° to 70° C.

The oximes of formula VI may be prepared in known manner by reacting the corresponding ketones with hydroxylamine. The ketones required for the reaction can in turn be obtained by reacting a Grignard compound of the formula VIII

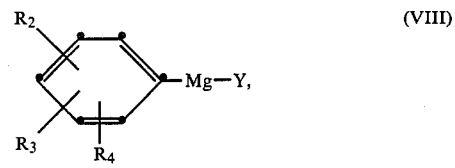

wherein Y is chlorine, bromine or iodine, and $R_2$, $R_3$ and $R_4$ are as defined above, with a carboxylic acid X—COOH, an acid chloride X—COCl or a nitrile X—CN, each derived from the radical X as defined above (cf. U.S. Pat. No. 3,748,361). Further, it is also possible to obtain ketones suitable for preparing the oximes of formula VI by reacting a benzene of the formula IX

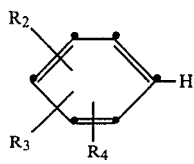

in which $R_2$, $R_3$ and $R_4$ are as defined above, with a carboxylic acid chloride X—COCl derived from the radical X as defined above, in the presence of aluminum chloride.

Examples of oximes of the formula VI which are suitable for obtaining the novel oxime ethers of the formula I are:
1-phenyl-1-hydroximino-2,2,2-trifluoroethane
1-(4-methylphenyl)-1-hydroximino-2,2,2-trifluoroethane
1-(4-chlorophenyl)-1-hydroximinp-2,2,2-trifluoroethane
1-(4-fluorophenyl)-1-hydroximino-2,2,2-trifluoroethane
1-(4-trifluoromethylphenyl)-1-hydroximino-2,2,2-trifluoroethane
1-(3-trifluoromethylphenyl)-1-hydroximino-2,2,2-trifluoroethane
1-(4-methoxyphenyl)-1-hydroximino-2,2,2-trifluoroethane
1-(4-trifluoromethoxyphenyl)-1-hydroximino-2,2,2-trifluoroethane
1-(3-nitrophenyl)-1-hydroximino-2,2,2-trifluoroethane
1-(3,4-dimethylphenyl)-1-hydroximino-2,2,2-trifluoroethane
1-(3,4-dichlorophenyl)-1-hydroximino-2,2,2-trifluoroethane
1-(4-chlorophenyl)-1-hydroximino-2,2-difluoroethane
1-(4-chlorophenyl)-1-hydroximino-2-chloro-2,2-difluoroethane
1-(4-methoxyphenyl)-1-hydroximino-2-chloro-2,2-difluoroethane
1-(4-trifluoromethoxyphenyl)-1-hydroximino-2-chloro-2,2-difluoroethane
1-(3-nitrophenyl)-1-hydroximino-2-chloro-2,2-difluoroethane
1-phenyl-1-hydroximino-2,2,3,3,3-pentafluoropropane
1-(4-methylphenyl)-1-hydroximino-2,2,3,3,3-pentafluoropropane
1-(4-chlorophenyl)-1-hydroximino-2,2,3,3,3-pentafluoropropane
1-(3-nitrophenyl)-1-hydroximino-2,2,3,3,3-pentafluoropropane
1-phenyl-1-hydroximino-2,2,3,3,4,4,4-heptafluorobutane
1-(4-chlorophenyl)-1-hydroximino-2,2,3,3,4,4,4-heptafluorobutane
1-(2-chlorophenyl)-1-hydroximino-2,2,2-trifluoroethane
1-(2-fluorophenyl)-1-hydroximino-2,2,2-trifluoroethane.

The haloalkyl ethers of formula VII can be prepared by reacting a halogenated alkanol of the fomula VIIa

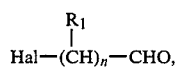

wherein n, Hal and $R_1$ are as defined above, in known manner, with a $C_1$–$C_4$ alkanol or mercaptan, or with a corresponding 1,2-, 1,3-, 1,4- or 1,5-alkanediol, a 1,4-alkenyldiol or with a corresponding dimercaptan.

Examples of suitable haloacetals of the formula III are:
1,1-dimethoxy-2-bromoethane
1,1-dimethoxy-2-bromopropane
1,1-diethoxy-2-bromoethane
1,1-dimethoxy-3-bromopropane
1,1-diethoxy-3-bromobutane
1,3-dioxolan-2-ylmethyl bromide
1-(1,3-dioxolan-2-yl)-1-bromoethane
1-(1,3-dioxolan-2-yl)-2-bromoethane
1-(1,3-dioxolan-2-yl)-2-bromopropane
4,5-dimethyl-1,3-dioxolan-2-ylmethyl bromide
4,4,5,5-tetramethyl-1,3-dioxolan-2-ylmethyl bromide
4,4-dimethyl-1,3-dioxolan-2-ylmethyl bromide
1-(4,5-dimethyl-1,3-dioxolan-2-yl)-1-bromoethane
1-(4,5-dimethyl-1,3-dioxolan-2-yl)-2-bromoethane
1-(4,5-dimethyl-1,3-dioxolan-2-yl)-2-bromopropane
1,3-dioxan-2-ylmethyl bromide
1-(1,3-dioxan-2-yl)-1-bromoethane
1-(1,3-dioxan-2-yl)-2-bromoethane
1-(1,3-dioxan-2-yl)-2-bromopropane
5,5-dimethyl-1,3-dioxan-2-ylmethyl bromide
4,4-dimethyl-1,3-dioxan-2-ylmethyl bromide
4,4,6-trimethyl-1,3-dioxan-2-ylmethyl bromide
1-(4,4,6-trimethyl-1,3-dioxan-2-yl)-1-bromoethane
1-(5,5-dimethyl-1,3-dioxan-2-yl)-1-bromoethane
1-(5,5-dimethyl-1,3-dioxan-2-yl)-2-bromoethane
1-(5,5-dimethyl-1,3-dioxan-2-yl)-2-bromopropane.

The above reactive acetals are a non-limitative selection. They can be prepared e.g. by reacting bromoacetaldehyde dimethyl or diethyl acetals with 1,2-, 1,3-, 1,4- or 1,5-alkanediols, or 1,2-, 1,3-, 1,4- or 1,5-alkanediols, which diols may be substituted by methyl, chloromethyl, $C_1$–$C_4$ alkoxymethyl, $C_2$–$C_4$ alkenyloxymethyl or nitro.

Examples of suitable diols, dimercaptans or mixed mercapto alcohols are the following:

| | |
|---|---|
| 1,2-propanediol | (+) R—1,2-butanediol |
| (+) S—1,2-propanediol | (−) S—1,2-butanediol |
| (−) S—1,2-propanediol | 1,2-butanediol |
| 3-fluoro-1,2-propanediol | 1,3-butanediol |
| 3-chloro-1,2-propanediol | 1,4-butanediol |
| 3-bromo-1,2-propanediol | meso-2,3-butanediol |
| 3-iodo-1,2-propanediol | (−)-2S,3S 2,3-butanediol |
| 3-methoxy-1,3-propanediol | 1-butene-2,3-diol |
| 3-ethoxy-1,3-propanediol | 2,3-pentanediol |
| 3-isopropoxy-1,3-propanediol | 2-methyl-1,2-butanediol |
| 3-nitro-1,3-propanediol | 2-methyl-2,3-butanediol |
| 3-allyloxy-1,2-propanediol | 2-methallyloxy-1,2-propanediol |
| 3-propargyloxy-1,2-propanediol | 3-acetoxy-1,3-propanediol |
| 3-methylmercapto-1,2-propanediol | 3-chloroallylmercapto-1,2-propanediol glycerol |

1,3-propanediol
2-chloro-1,3-propanediol
2-bromo-1,3-propanediol
2-butene-1,4-diol
2-hydroxymethyl-2-propen-1-ol
2-hydroxymethyl-2-buten-1-ol
2-methyl-1,2-propanediol
3-chloro-2-methyl-1,2-propanediol
3-chloro-2-chloromethyl-1,2-propanediol
3-methyl-1,3-propanediol
2-methyl-2-nitro-1,3-propanediol
1,2-pentanediol
2,4-pentanediol 2-methyl-1,3-butanediol
2-methyl-2,4-butanediol
2-methyl-3,4-butanediol
1,4-dichloro-2-methyl-2,3-butanediol
4-iodo-2-methyl-2,3-butanediol
2,2-dimethyl-1,3-propanediol
2,4-hexanediol
3-methyl-2,4-pentanediol
1,5-hexane-3,4-diol
2-propanol-1-thiol
3-propanol-1-thiol
1,3-propane-dithiol
2,3-butane-dithiol
1-methyl-1,2-propane-dithiol 1-butene-2,3-dithiol
2-methyl-1,2-butanedithiol
2-ethyl-1,3-propanediol
4-bromo-2-methyl-2,3-butanediol
2,2-dimethyl-1,3-propanediol
2,2-bis-chloromethyl-1,3-propanediol
2-methyl-2,3-pentanediol
2,2-dimethyl-3,4-butanediol
2-ethanol-1-thiol
3-chloro-2-propanol-1-thiol
1,2-ethane-dithiol
1,2-butanedithiol
1,4-butenedithiol
2-butene-1,4-dithiol
2,3-pentane-dithiol
2-methyl-2,3-butanedithiol.

Compounds of the formula I can also be converted into other compounds. A 4,7-dihydro-1,3-dioxepine compound of formula I is prepared e.g. by the following reaction scheme:

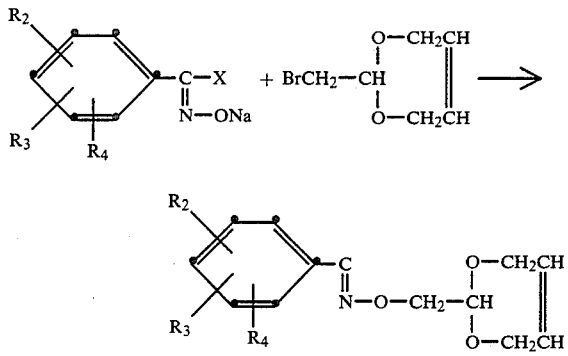

According to a process described in Tetrahedron 21 (1980) 4922, the double bond is displaced by treating this compound at 100° C. with a ruthenium catalyst to form the corresponding 4,5-dihydro-1,3-dioxepine compound.

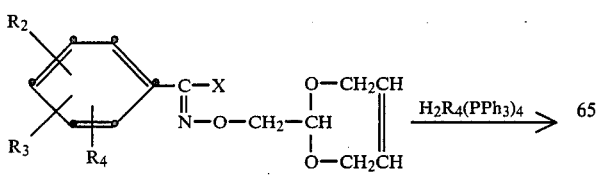

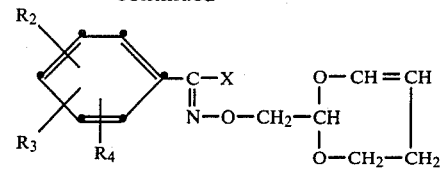

To prepare the compounds of formula I, wherein Y is an alkyl or phenyl radical, the oxime salt of formula VI is reacted with a haloalkyl or phenyl ketal or thioketal, preferably with a bromo- or iodoketal, in accordance with the reaction scheme:

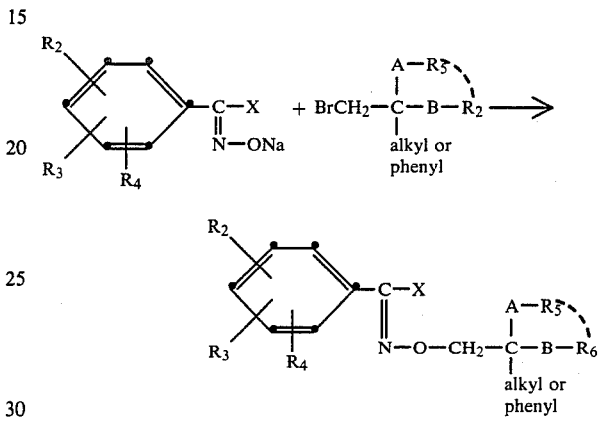

Such haloketals are known from the literature. The α-bromacetone ketal can be prepared by the method described in Synthesis 1982 309, and other ketals, e.g. 1-bromopinacoline ethylene ketal or 1-bromoacetophenone ethylene ketal, may be prepared by the method described in J. prakt. Chemie 156 (1940) 121.

These compounds can also be obtained by condensation of oximes e.g. with haloketones such as bromacetone and subsequent ketalisation. A further method of preparing such compounds is e.g. the reaction with 2-methoxy-1,3-dioxolane as described in J. of Med. Chem. 25 (1982), 12, in accordance with the scheme:

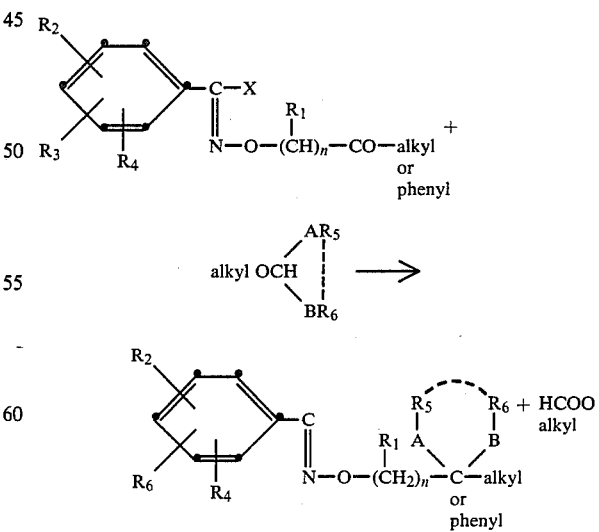

The orthoesters of formula I (compounds in which Y is alkoxy) are prepared by reacting the oxime salt of formula VI with a halo-orthocarboxylic acid ester, e.g.

triethyl monobromo-orthoacetate, in accordance with J. Am. Soc. 59 (1937), 1273 and with the reaction scheme:

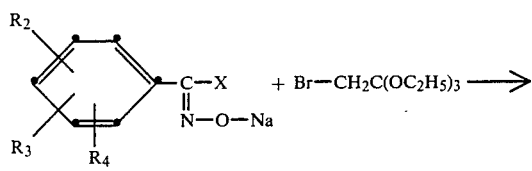

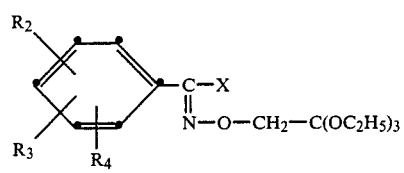

Reaction of the halo-orthocarboxylates with suitable diols and mercaptans gives mixed esters such as glycol ethyl bromo-orthoacetate or dimethylthioethyl bromo-orthoacetate, which are suitable for reaction with the oxime salt of formula VI. Orthoesters of formula I can also be prepared e.g. by a method described in J. Am. Chem. Soc. 77 (1955), 4574, by reacting a cyanoalkyl oxime to give the iminoester hydrochloride and subsequently condensing this latter compound with a diol, e.g. glycol, according to the reaction scheme:

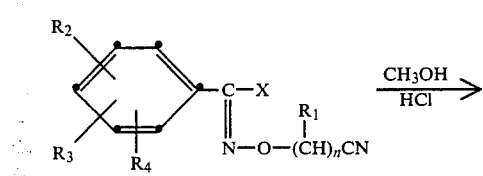

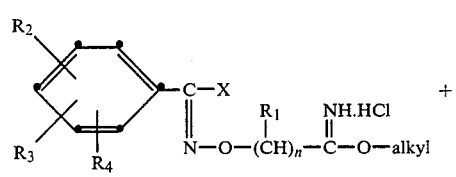

HAC$_2$H$_4$BH $\longrightarrow$

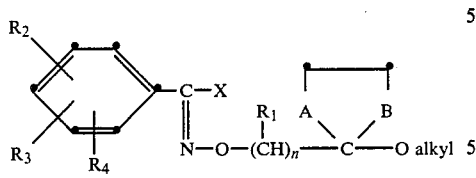

Compounds of formula I, wherein A and/or B are sulfur, are prepared by methods similar to those employed for preparing the acetal compounds. Simple thioacetals, thioketals, dithiolanes and dithianes can be prepared by using thiols or dithiols. Particularly suitable, however, is the transesterification of aliphatic dialkyl acetals e.g. with a mercaptan, e.g. the transesterification of an oxime dimethoxyethylester with a mercaptan such as 1,2-ethylenedithiol in the following reaction scheme:

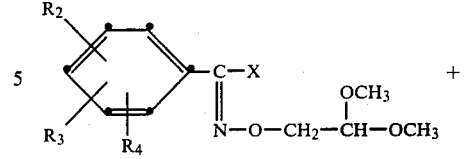

HSC$_2$H$_4$SH $\longrightarrow$

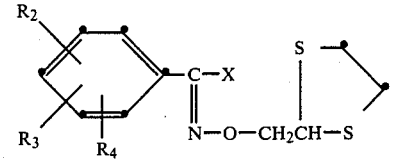

These same cyclic thioacetal compounds can also be obtained by reacting the corresponding acetals with dithiols according to the reaction scheme:

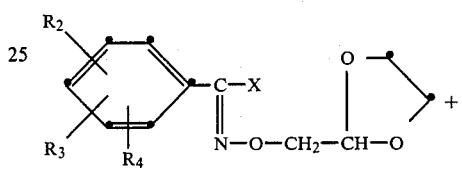

HSC$_2$H$_4$SH $\longrightarrow$

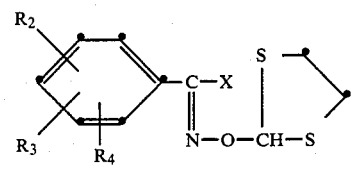

Compounds of formula I, wherein A is oxygen, B is methylene and Y is hydrogen, and R$_5$ and R$_6$ together form a hydrocarbon bridge member, can be prepared by reacting the oxime salts of formula VI with corresponding 2-α-haloalkyl oxygen rings such as 2-bromomethylfurane, 2-bromomethylpyrane, 2-bromoethyloxepane, according to the reaction scheme:

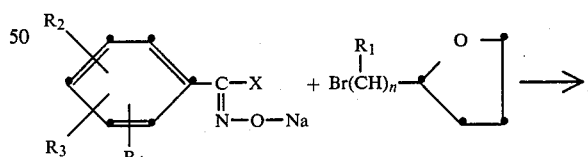

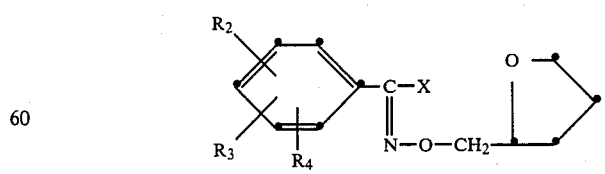

Instead of starting from oxime salts of formula VI as in the preceding processes, it is also possible to start from the ketones on which these oximes are based and reacting them with O-substituted hydroxylamines in accordance with the reaction scheme:

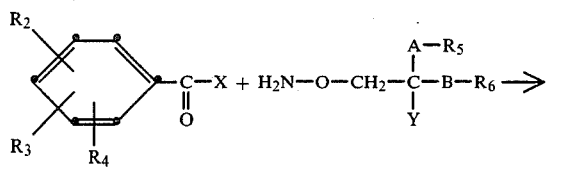

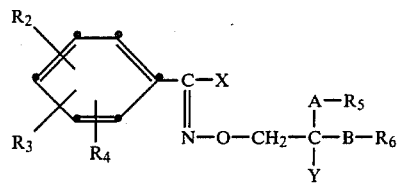

Further, such phenones can be transacetalised with correspondingly substituted acetone oxime ethers to give compounds of the formula I

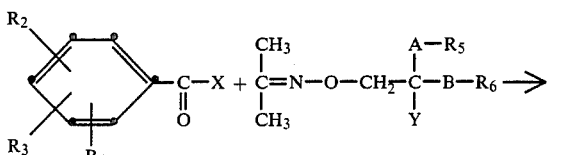

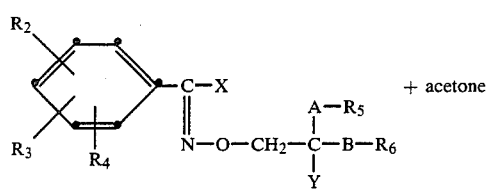

The novel oxime ethers of formula I are most suitable for protecting cultivated plants from damage caused by agrochemicals. This protection extends in particular to herbicides of different compound classes, including 1,3,5-triazines, 1,2,4-triazines, phenylurea derivatives, carbamates, thiocarbamates, phenoxyacetates, phenoxypropionates, haloacetanilides, halophenoxyacetates, substituted phenoxyphenoxyacetates and phenoxyphenoxypropionates, substituted pyridyloxyphenoxyacetates and pyridyloxyphenoxypropionates, benzoic acid derivatives etc., where these compounds are not tolerated or are insufficiently tolerated by cultivated plants. The novel oxime ethers of formula I are suitable in particular for protecting cultivated plants from the harmful effects of haloacetanilides and thiocarbamates. They can therefore be termed antidotes or also safeners with respect to their use in combination with the herbicides referred to above.

The compounds of the formula I exist in different isomeric forms.

As oxime derivatives, these compounds are obtained in the syn- and anit-form or as mixtures thereof (E- and Z-form, cf. R. S. Cohn et al., Ang. Chemie Int. Ed. 5 (1966), 385, or Experientia 12 (1956), p. 81).

Depending on the substitution of the compounds of formula I, an asymmetrical carbon atom is present and two enantiomers may be obtained. In general, a mixture of both enantiomers is obtained, which mixture can be resolved into the optional antipodes in conventional manner.

The monosubstituted dioxolanes and dioxanes lead to further cis-trans-isomers or mixtures thereof. Disubstituted dioxolanes lead to cis-syn-isomers, cis-anti-isomers and trans-isomers or mixtures thereof. The number of isomers can be reduced by choice of starting materials, e.g. by using the pure Z-form of the oximes. The present invention also relates to these different isomers and to mixtures thereof.

Depending on the end use, the safener or antidote of the formula I can be used for pretreating seeds of the cultivated plant (dressing of the seeds or seedlings) or it can be added to the soil before or after sowing. However, it can also be applied pre- or post-emergence by itself alone or together with the herbicide. The treatment of the plant or seeds with the antidote can therefore in principle be carried out independently of the time of application of the phytotoxic chemical. It can, however, also be carried out by simultaneous application of phytoxic chemical and antidote (tank mixture). The pre-emergence treatment includes both treatment of the crop area before sowing (ppi=pre-plant incorporation) and treatment of the crop areas after sowing but before emergence of the plants.

The rates of application of the antidote with respect to the herbicide depend largely on the mode of application. Where a field treatment is carried out, either simultaneously as tank mixture or with separate application of herbicide and antidote, the ratio of antidote to herbicide is in the range from 1:100 to 5:1. Full protective action is usually obtained at a ratio of antidote to herbicide of 1:1 to 1:20. When dressing seeds and taking similar specific protective measures, however, much lower amounts of antidote are required compared with e.g. the amounts of herbicide later employed per hectare of crop area. For seed dressing, 0.1 to 10 g of antidote per kg of seeds are required, with the preferred amount being from 1 to 2 grams. If it is desired to apply the antidote shortly before sowing by seed pretreatment, antidote solutions which contain the active ingredient in a concentration of 1 to 10,000 ppm are used. Full protective action is normally obtained with antidote concentrations of 100 to 1000 ppm.

As a rule there is a substantial interval of time between protective measures such as seed dressing and treatment of seedlings with an antidote of the formula I and the possible later field treatment with agricultural chemicals. Pretreated seeds and plants can later come in contact with different chemicals in agriculture, horticulture and forestry. Accordingly, the invention relates to plant protection compositions which contain an antidote of the formula I as active ingredient, together with conventional carriers. If appropriate, such compositions may be additionally mixed with the chemical against whose effects it is desired to protect the cultivated plant.

Cultivated plants within the scope of this invention are all plants which, in any form, can be harvested (seeds, roots, stalks, tubers, leaves, blossoms) and from which extracts can be obtained (oils, sugar, starch, protein) and which are cultivated for this purpose.

To these plants belong e.g. all species of cereals such es wheat, rye, barley, oats and, in particular, rice, sorghum, maize, and also cotton, sugar beet, sugar cane, soybeans, beans, and peas.

The antidote can be employed wherever it is desired to protect a cultivated plant of the kind indicated above from the harmful effects of an agricultural chemical. As already mentioned, possible agricultural chemicals are primarily herbicides of the most widely varying compounds classes, in particular haloacetanilides and thiocarbamates.

Numerous haloacetanilides whose harmful effects on cultivated plants can be antagonised with the novel oxime ethers of the formula I are known in the art (q.v. German patent application Nos. 2 305 495, 2 328 340, 2 212 268, 2 726 252 and 2 805 757, and U.S. Pat. Nos. 3,946,044, 4,022,608 and 4,039,314). Such haloacetanilides may be illustrated by the general formula XIV

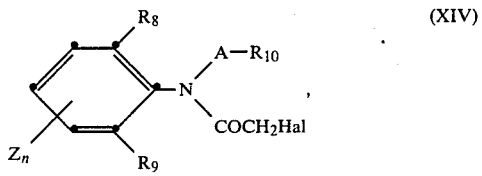

wherein Hal is halogen, preferably chlorine or bromine, each of $R_8$ and $R_9$ independently of the other is hydrogen, halogen, lower alkyl, alkoxy, alkylthio, haloalkyl, alkoxyalkyl or alkylthioalkyl, Z is hydrogen, halogen, lower alkyl, alkoxy, alkylthio, haloalkyl, alkoxyalkyl or alkylthioalkyl, which radicals Z are preferably in the 3-position with respect to the nitrogen atom, n is 0 to 3, A is alkylene, preferably methylene, 1,1-ethylene, and 1,2-ethylene which may be substituted by 1 to 2 lower alkyl groups, and $R_{10}$ is lower alkoxy, allyloxy, hydroxycarbonyl, alkoxycarbonyl, carbamoyl, N-alkylcarbamoyl, N,N-dialkylcarbamoyl, N-propargylcarbamoyl, ethynyl, 1,3-dioxolanyl, 2-tetrahydrofuranyl, cyano, an unsubstituted or substituted nitrogen-containing heterocyclic radical, alkanoyl, unsubstituted or substituted benzoyl, unsubstituted or substituted 1,3,4-oxadiazol-2-yl, 1,3,4-thiadiazol-2-yl, 1,3,4-triazol-3-yl or 1,3,4-triazol-1-yl.

Typical examples of such haloacetanilides are:
N-ethoxymethyl-N-chloroacetyl-2-ethyl-6-methylaniline
N-chloroacetyl-N-methoxymethyl-2,6-diethylaniline
N-chloroacetyl-N-(2-methoxyethyl)-2,6-dimethylaniline
N-(2-allyloxyethyl)-N-chloroacetyl-2,6-dimethylaniline
N-chloroacetyl-N-(2-n-propoxyethyl)-2,6-dimethylaniline
N-chloroacetyl-N-(2-isopropoxyethyl)-2,6-dimethylaniline
N-chloroacetyl-N-(2-methoxyethyl)-2-ethyl-6-methylaniline
N-chloroacetyl-N-(methoxyethyl)-2,6-diethylaniline
N-(2-ethoxyethyl)-N-chloroacetyl-2-ethyl-6-methylaniline
N-chloroacetyl-N-(2-methoxy-1-methylethyl)-2-methylaniline
N-chloroacetyl-N-(2-methoxy-1-methylethyl)-2,6-dimethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-methoxycarbonylmethyl-2,6-dimethylaniline
N-chloroacetyl-N-(2,2-diethoxyethyl)-2,6-dimethylaniline
N-chloroacetyl-N-(2-methoxy-1-methylethyl)-2,3-dimethylaniline
N-(2-ethoxyethyl)-N-chloroacetyl-2-methylaniline
N-chloroacetyl-N-(2-methoxyethyl)-2-methylaniline
N-chloroacetyl-N-(2-methoxy-2-methylethyl)-2,6-dimethylaniline
N-(2-ethoxy-2-methylethyl)-N-chloroacetyl-2-ethyl-6-methylaniline
N-chloroacetyl-N-(1-ethyl-2-methoxyethyl)-2,6-dimethylaniline
N-chloroacetyl-N-(2-methoxyethyl)-2-methoxy-6-methylaniline
N-n-butoxymethyl-N-chloroacetyl-2-tert-butylaniline
N-(2-ethoxyethyl-1-methylethyl)-2,6-dimethylaniline
N-chloroacetyl-N-(2-methoxyethyl)-2-chloro-6-methylaniline
N-(2-ethoxyethyl)-N-chloroacetyl-2-chloro-6-methylaniline
N-(2-ethoxyethyl)-N-chloroacetyl-2,3,6-trimethylaniline
N-chloroacetyl-1-(2-methoxyethyl)-2,3,6-trimethylaniline
N-chloroacetyl-N-cyanomethyl-2,6-dimethylaniline
N-but-3-yn-1-yl-N-chloroacetylaniline
N-chloroacetyl-N-propargyl-2-ethyl-6-methylaniline
N-chloroacetyl-N-(1,3-dioxolan-2-ylmethyl)-2,6-dimethylaniline
N-chloroacetyl-N-(1,3-dioxolan-2-ylmethyl)-2-ethyl-6-methylaniline
N-chloroacetyl-N-(1,3-dioxan-2-ylmethyl)-2-ethyl-6-methylaniline
N-chloroacetyl-N-(1,3-dioxan-2-ylmethyl)-2-ethyl-6-methylaniline
N-chloroacetyl-N-(2-furanylmethyl)-2,6-dimethylaniline
N-chloroacetyl-N-(2-furanylmethyl)-2-ethyl-6-methylaniline
N-chloroacetyl-N-(2-tetrahydrofuranylmethyl)-2,6-dimethylaniline
N-chloroacetyl-N-(N-propargylcarbamoylmethyl)-2,6-dimethylaniline
N-chloroacetyl-N-(N,N-dimethylcarbamoylmethyl)-2,6-dimethylaniline
N-(n-butoxymethyl)-N-chloroacetyl-2,6-diethylaniline
N-(2-n-butoxyethyl)-N-chloroacetyl-2,6-diethylaniline N-chloroacetyl-N-(2-methoxy-1,2-dimethylethyl)-2,6-dimethylaniline
N-chloroacetyl-N-isopropyl-2,3-dimethylaniline
N-chloroacetyl-N-isopropyl-2-chloroaniline
N-chloroacetyl-N-(1H-pyrazol-1-ylmethyl)-2,6-dimethylaniline
N-chloroacetyl-N-(1H-pyrazol-1-ylmethyl)-2-ethyl-6-methylaniline
N-chloroacetyl-N-(1H-1,2,4-triazol-1-ylmethyl)-2,6-dimethylaniline
N-chloroacetyl-N-(1H-1,2,4-triazol-1-ylmethyl)-2,6-diethylaniline
N-benzoylmethyl-N-chloroacetyl-2,6-dimethylaniline
N-benzoylmethyl-N-chloroacetyl-2-ethyl-6-methylaniline
N-chloroacetyl-N-(5-methyl-1,3,4-oxadiazol-2-yl)-2,6-diethylaniline
N-chloroacetyl-N-(5-methyl-1,3,4-oxadiazol-2-yl)-2-ethyl-6-methylaniline
N-chloroacetyl-N-(5-methyl-1,3,4-oxadiazol-2-yl)-2-tert-butylaniline
N-chloroacetyl-N-(4-chlorobenzoylmethyl)-2,6-dimethylaniline
N-chloroacetyl-N-(1-methyl-5-methylthio-1,3,4-triazol-2-ylmethyl)2,6-diethylaniline.

Further haloacetanilides whose harmful effects on cultivated plants can be antagonised by the novel oxime ethers of the formula I are listed in R. Wegler, Chemie der Pflanzenschutz- und Schädlingsbekämpfungsmittel, Vol. 8, pp. 90–93 and pp. 322–327.

Numerous herbicidal thiocarbamates whose phytotoxic action on cultivated plants can be antagonised by the novel oxime ethers of the formula I are also known (q.v. for example U.S. Pat. Nos. 2,913,327, 3,037,853, 3,175,897, 3,185,720, 3,198,786, 3,582,314 and 3,846,115). The protective action of the novel oxime ethers of the formula I can be utilised particularly when applying thiocarbamates in cereals, rice or sorghum.

The thiocarbamates against whose phytotoxic action cultivated plants such as cereals, rice and sorghum may particularly be protected, have the general formulae XV and XVI:

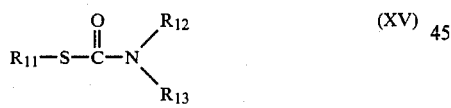
(XV)

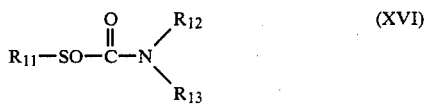
(XVI)

wherein $R_{11}$ is lower alkyl, alkenyl, chloroallyl, dichloroallyl, trichloroallyl, benzyl or 4-chlorobenzyl, $R_{12}$ is $C_2$–$C_4$ alkyl and $R_{13}$ is $C_2$–$C_4$ alkyl or cyclohexyl, and $R_{12}$ and $R_{13}$ together with the nitrogen atom to which they are attached can form a hexahydro-1H-azepine, decahydroquinoline or 2-methyldecahydroquinoline ring.

Typical individual representatives of such thiocarbamates are:
S-ethyl-N,N-dipropylthiocarbamate
S-ethyl-N,N-diisobutylthiocarbamate
S-2,3-dichloroallyl-N,N-diisopropylthiocarbamate
S-propyl-N-butyl-N-ethylthiocarbamate
S-2,3,3-trichloroallyl-N,N-diisopropylthiocarbamate
S-propyl-N,N-dipropylthiocarbamate
S-ethyl-N-ethyl-N-cyclohexylthiocarbamate
S-ethyl-N-hexahydro-1H-azepine-1-carbothioate
S-isopropyl-N,N-hexamethylene-thiocarbamate
S-(p-chlorobenzyl)-N,N-diethylthiocarbamate
N-ethylthiocarbonyl-cis-decahydroquinoline
N-propylthiocarbonyl-decahydroquinaldine
S-ethyl-N,N-bis(n-butyl)-thiocarbamate
S-tert-butyl-N,N-bis(n-propyl)-thiocarbamate.

In addition to the chloroacetanilides and thiocarbamates, herbicides of other compound classes are also possible, e.g.:

Triazines and triazinones: 2,4-bis(isopropylamino)-6-methylthio-1,3,5-triazine ("prometryn"), 2,4-bis(ethylamino)-6-methylthio-1,3,5-triazine ("symetryn"), 2-(1',2'-dimethylpropylamino)-4-ethylamino-6-methylthio-1,3,5-triazine ("dimethametryn"), 4-amino-6-tert-butyl-4,5-dihydro-3-methylthio-1,2,4-triazin-5-one ("metribuzin"), 2-tert-butylamino-4-ethylamino-6-methylthio-1,3,5-triazine ("terbutryn"), 2-chloro-4-tert-butylamino-6-ethylamino-1,3,5-triazine ("terbuthylazin"), 2-chloro-4-isopropylamino-6-ethylamino-1,3,5-triazine ("atrazin"), 2-tert-butylamino-4-alkylamino-6-methoxy-1,3,5-triazine ("terbumeton"), 2-chloro-4,6-bis(ethylamino)-1,3,5-triazine ("simazin"), 2-ethylamino-4-isopropylamino-6-methylthio-1,3,5-triazine ("ametryn").

Ureas: 1-(benzothiazol-2-yl)-1,3-dimethylurea; phenylureas such as 3-(3-chloro-p-tolyl)-1,1-dimethylurea ("chlorotoluron"), 1,1-dimethyl-3-(α,α,α-trifluoro-m-tolyl)urea ("fluometuron"), 3-(4-bromo-3-chlorophenyl)-1-methoxy-1-methylurea ("chlorbromuron"), 3-(4-bromophenyl)-1-methoxy-1methylurea ("metobromuron"), 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethylurea ("diuron"), 3-(4-chlorophenyl)-1,1-dimethylurea ("monuron"), 3-(3-chloro-4-methoxyphenyl)-1,1-dimethylurea ("metoxuron"); sulfonylureas such as N-(2-chlorophenylsulfonyl)-N'-(4-methoxy-6-methyl-1,3,5-triazin-2-yl)urea, N-(2-methoxycarbonylphenylsulfonyl)-N'-(4,6-dimethylpyrimidin-2-yl)urea, N-[2-(2-butenyloxy)phenylsulfonyl]-N'-(4-methoxy-6-methyl-1,3,5-triazin-2-yl)urea, as well as the sulfonylureas cited in European patent publications 44808 and 44809.

Chloroacetamides: N-[1-isopropyl-2-methylpropan-1-yl(1)]-N-(2'-methoxyethyl)-chloroacetamide.

Diphenyl ethers and nitrodiphenyl ethers: 2,4-dichlorophenyl-4'-nitrophenyl ether ("nitrofen"), 2-chloro-1-(3'-ethoxy-4'-nitrophenoxy)-4-trifluoromethylbenzene ("oxyfluorfen"), 2',4'-dichlorophenyl-3-methoxy-4-nitrophenyl ether ("chlormethoxynyl"), methyl 2-[4'-(2",4"-dichlorophenoxy)phenoxy]propionate, N-(2'-phenoxyethyl)-2-[5'(2"-chloro-4"'-trifluoromethylphenoxy)-phenoxy]propionamide, 2-methoxyethyl 2-[2-nitro-5-(2-chloro-4-trifluoromethylphenoxy)phenoxy]propionate, 2-chloro-4-trifluoromethylphenyl-3'-oxazolin-2'-yl-4'-nitrophenyl ether.

Benzoic acid derivatives: methyl-5-(2',4'-dichlorophenoxy)-2-nitrobenzoate ("bifenox"), 5-(2'-chloro-4'-trifluoromethylphenoxy)-2-nitrobenzoic acid ("acifluorfen"), 2,6-dichlorobenzonitrile ("dichlobenil").

Nitroanilines: 2,6-dinitro-N,N-dipropyl-4-trifluoromethylaniline ("trifluralin"), N(1'-ethylpropyl)-2,6-dinitro-3,4-xylidine ("pendimethalin").

Oxadiazolones: 5-tert-butyl-3(2',4'-dichloro-5'-isopropoxyphenyl)-1,3,4-oxadiazol-2-one ("oxadiazon").

Phosphates: S-2-methylpiperidinocarbonylmethyl-0,0-dipropylphosphorodithioate ("piperophos").

Pyrazoles: 1,3-dimethyl-4-(2',4'-dichlorobenzoyl)-5-(4'-tolylsulfonyloxy)pyrazole.

α-(Phenoxyphenoxy)propionic acid derivatives and α-Pyridyl-2-oxyphenoxy)propionic acid derivatives The amount of antidote employed varies from about 0.01 to about 15 parts by weight per part by weight of herbicide. The most suitable ratio in respect of optimum action on the particular cultivated plant is established from case to case, i.e. depending on the type of herbicide employed.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents", Chemical Publishing Co., Inc. New York, 1980.

These compositions usually contain 0.1 to 99%, preferably 0.1 to 95%, of a compound of the formula I, 1 to 99% of a solid or liquid adjuvant, and 0 to 25%, preferably 0.1 to 25%, or a surfactant.

Whereas commercial products are preferably formulated as concentrates, the end user will normally employ dilute formulations.

The compositions may also contain further ingredients, such as stabilisers, antifoams, viscotity regulators, binders, tackifiers as well as fertilisers or other active ingredients in order to obtain special effects.

The invention is illustrated in more detail by the following Examples, without implying any restriction to what is described therein. Parts and percentages are by weight.

EXAMPLE 1

Preparation of
1-(4-chlorophenyl)-1-(1,3-dioxolan-2-ylmethoxyimino)-2,2,2-trifluoroethane (compound 40)

(a) In a 100 ml round flask, 1.2 g (0.05 mole) of metallic sodium are dissolved in 50 ml of absoute ethanol, and then 11.2 g (0.05 mole) of 1-(4-chlorophenyl)-1-hydroximino-2,2,2-trifluoroethane are added. When the addition is complete, the reaction mixture is stirred initially for half an hour at room temperature and then the solvent is removed by evaporation. With stirring, 8.4 g (0.05 mole) of 2-bromomethyl-1,3-dioxolane are added dropwise to the solution of the residue in 50 ml of dimethylsulfoxide and the batch is subsequently stirred for 4 hours at 60° to 70° C. The resultant suspension is cooled and poured into a mixture of ice and water. The reaction product is obtained from the mixture by extraction with methylene chloride. The extract is dried over sodium sulfate and the solvent is removed by evaporation. The crude product is an orange oil which is purified by distillation in a high vacuum. Yield: 12.5 g (80.6% of theory) of 1-(4-chlorophenyl)-1-(1,3-dioxolan-2-ylmethoximino)-2,2,2-trifluoroethane in the form of a colourless oil with a boiling point of 105° to 108° C./0.1 mbar.

(b) The starting 1-(4-chlorophenyl)-hydroximino-2,2,2-trifluoroethane is prepared as follows:

A mixture of 417 g (2 moles) of 4-chloro-$\omega,\omega,\omega$-trifluoroacetophenone, 139 g (2 moles) of hydroxylamino hydrochloride and 500 ml of pyridine is stirred for 15 hours at room temperature. The pyridine is subsequently removed by distillation and the oily residue is stirred in ice/water. The product is extracted with methylene chloride and the extract is dried over sodium sulfate and the solvent removed by evaporation, affording 438 g (98% of theory) of 1-(4-chlorophenyl)-1-hydroximino-2,2,2-trifluoroethane in the form of an oil.

EXAMPLE 2

Preparation of
1-phenyl-1-(1,3-dioxolan-2-ylmethoximino)-2,2,2-trifluoroethane (compound 38)

13.8 (0.07 mole) of 1-(hydroximino)-1-phenyl-2,2,2-trifluoroethane are stirred into a solution of 1.5 g (0.07 mole) of metallic sodium in 50 ml of absolute ethanol and the solvent is subsequently evaporated off. With stirring, 6.7 g (0.10 mole) of 2-bromomethyl-1,3-dioxolane are added dropwise to the solution of the residue in 50 ml of dimethylsulfoxide. When the addition of 2-bromomethyl-1,3-dioxolane is complete, the reaction mixture is stirred initially for 4 hours at 60° to 70° C. and then the resultant suspension is poured into a mixture of ice and water. The product is extracted with methylene chloride and the extract is dried over sodium sulfate and the solvent is removed by evaporation. The crude product is an orange oil which is purified by distillation in a high vacuum. Yield: 15 g (78% of theory) of 1-phenyl-1-(1,3-dioxolan-2-ylmethoximino)-2,2,2-trifluoroethane with a boiling point of 89° to 90° C./0.1 mbar.

EXAMPLE 3

Preparation of
1-(4-chlorophenyl)-1-(2,2-diethoxyethoximino)-2,2,2-trifluoroethane (compound 11)

25.6 g (0.1 mole) of 1-hydroximino-1-(4-chlorophenyl)-2,2,2-trifluoroethane are added dropwise to a solution of 2.3 g (0.1 mole) of metallic sodium in 50 ml of absolute ethanol. When the addition is complete, the reaction mixture is stirred for half an hour at room temperature and then the solvent is removed by evaporation. With stirring, 29.7 g (0.15 mole) of 2-bromacetaldehyde diethyl acetal are added to the solution of the residue in 50 ml of dimethylsulfoxide. When the addition is complete, the reaction mixture is stirred for 4 hours at 60° to 70° C. and then poured into a mixture of ice and water. The crude oily product obtained after extraction with methylene chloride, drying the extract over sodium sulfate and removing the solvent by evaporation is purified by distillation in a high vacuum.

Yield: 20.5 g (73.5% of theory) of 1-(4-chlorophenyl)-1-(2,2-diethoxyethoximino)-2,2,2-trifluoroethane in the form of a colourless oil with a boiling point of 95° to 97° C./0.02 mbar.

EXAMPLE 4

Preparation of
1-(4-chlorophenyl)-1-(2,2-dimethoxyethoximino)-2,2,2-trifluoroethane (compound 2)

25.6 g (0.1 mole) of 1-hydroximino-1-(4-chlorophenyl-2,2,2-trifluoroethane are added dropwise to a solution of 2.3 g (0.1 mole) of metallic sodium in 50 ml of absolute ethanol. When the addition is complete, the reaction mixture is stirred for half an hour at room temperature and then the solvent is removed by evaporation. With stirring, a solution of 33.8 g (0.2 mole) of 2-bromacetaldehyde demethyl acetal in 60 ml of dimethylsulfoxide are added to the solution of the residue in 50 ml of dimethylsulfoxide. When the addition is complete, the reaction mixture is stirred for 4 hours at 60° to 70° C., then cooled and poured into a mixture of ice and water. The crude oily product obtained after extraction with methylene chloride, drying the extract over sodium sulfate and removing the solvent by evaporation is purified by distillation in a high vacuum. Yield: 22 g (70.5% of theory) of 1-(4-chlorophenyl)-1-(2,2-dimethoxyethoximino)-2,2,2-trifluoroethane in the form of a colourless oil with a boiling point of 96° to 98° C./0.02 mbar.

The following compounds are prepared in accordance with the preceding Examples

TABLE 1

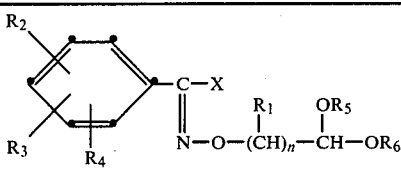

| No. | X | n | R₁ | R₂ | R₃ | R₄ | R₅ | R₆ | Physical data (°C.) |
|---|---|---|---|---|---|---|---|---|---|
| 1 | $CF_3$ | 1 | H | H | H | H | $CH_3$ | $CH_3$ | b.p. 66–68°/0.03 mbar |
| 2 | $CF_3$ | 1 | H | H | 4-Cl | H | $CH_3$ | $CH_3$ | b.p. 96–98°/0.02 mbar |
| 3 | $CF_3$ | 1 | H | H | H | H | $C_2H_5$ | $C_2H_5$ | b.p. 77–78°/0.04 mbar |
| 4 | $CF_3$ | 1 | H | H | 4-F | H | $CH_3$ | $CH_3$ | b.p. 67–68°/0.01 mbar |
| 5 | $CF_3$ | 1 | H | H | 4-Cl | H | $n-C_3H_7$ | $n-C_3H_7$ | |
| 6 | $CClF_2$ | 1 | H | H | 4-$OCH_3$ | H | $n-C_4H_9$ | $n-C_4H_9$ | |
| 7 | $CClF_2$ | 2 | H | H | H | H | $C_2H_5$ | $C_2H_5$ | |
| 8 | $CF_3$ | 1 | $CH_3$ | H | 3-$NO_2$ | H | $CH_3$ | $CH_3$ | |
| 9 | $C_2F_5$ | 1 | $CH_3$ | 3-Cl | 4-Cl | H | $C_2H_5$ | $C_2H_5$ | |
| 10 | $CClF_2$ | 1 | $CH_3$ | H | 2-Cl | H | $C_2H_5$ | $C_2H_5$ | |
| 11 | $CF_3$ | 1 | H | H | 4-Cl | H | $C_2H_5$ | $C_2H_5$ | b.p. 95–97°/0.02 mbar |
| 12 | $CF_3$ | 1 | $CH_3$ | H | 3-$NO_2$ | H | $C_2H_5$ | $C_2H_5$ | |
| 13 | $C_2F_5$ | 1 | $CH_3$ | H | 4-$OCH_3$ | H | $CH_3$ | $CH_3$ | |
| 14 | $C_2F_5$ | 1 | $CH_3$ | H | 4-$OCF_3$ | H | $i-C_3H_7$ | $i-C_3H_7$ | |
| 15 | $CF_3$ | 1 | H | H | 2-Cl | H | $i-C_3H_7$ | $i-C_3H_7$ | |
| 16 | $CF_3$ | 1 | $CH_3$ | H | H | H | $CH_2-CH=CH_2$ | $CH_2-CH=CH_2$ | |
| 17 | $C_2F_5$ | 1 | H | H | 4-Cl | H | $CH_3$ | $CH_3$ | |
| 18 | $CF_3$ | 1 | H | H | 4-$OCH_3$ | H | $C_2H_5$ | $C_2H_5$ | |
| 19 | $CF_3$ | 1 | H | H | 4-$OCF_3$ | H | $n-C_3H_7$ | $n-C_3H_7$ | |
| 20 | $CF_3$ | 1 | $CH_3$ | H | 4-$SO_2-CF_3$ | H | $CH_3$ | $CH_3$ | |
| 21 | $CClF_2$ | 1 | H | H | 4-Cl | H | $C_2H_5$ | $C_2H_5$ | |
| 22 | $CF_3$ | 1 | $CH_3$ | H | 3-$CF_3$ | H | $CH_3$ | $CH_3$ | |
| 23 | $C_2F_5$ | 1 | H | H | 4-$OCH_3$ | H | $CH_2-CH=CH_2$ | $CH_2-CH=CH_2$ | |
| 24 | $C_3G_7$ | 1 | H | H | 4-Cl | H | $C_2H_5$ | $C_2H_5$ | |
| 25 | $CF_3$ | 1 | $CH_3$ | H | 3-$CF_3$ | H | $n-C_3H_7$ | $n-C_3H_7$ | |
| 26 | $CF_3$ | 1 | $C_2H_5$ | H | 3-$NO_2$ | H | $C_2H_5$ | $C_2H_5$ | |
| 27 | $CF_3$ | 2 | H | H | 2-F | H | $CH_3$ | $CH_3$ | |
| 28 | $CF_3$ | 1 | $i-C_3H_7$ | H | 2-Cl | H | $C_2H_5$ | $C_2H_5$ | |
| 29 | $CF_3$ | 2 | $CH_3$ | H | 3-$CF_3$ | H | $C_2H_5$ | $C_2H_5$ | |
| 30 | $CF_3$ | 1 | H | H | 3-$NO_2$ | H | $C_2H_5$ | $C_2H_5$ | |
| 31 | $CF_3$ | 1 | H | H | 4-$OCH_3$ | H | $CH_2-CH=CH_2$ | $CH-CH=CH_2$ | |
| 32 | $CF_3$ | 1 | H | H | 4-$SO_2CF_3$ | H | $CH_3$ | $CH_3$ | |
| 33 | $C_2F_5$ | 1 | H | H | 3-$CF_3$ | H | $CH_2-\underset{\underset{CH_3}{\mid}}{C}=CH_2$ | $CH_2-\underset{\underset{CH_3}{\mid}}{C}=CH_2$ | |
| 34 | $CF_3$ | 1 | H | H | 4-Cl | H | $CH_2-CH=CH_2$ | $CH_2-CH=CH_2$ | |
| 35 | $C_2F_5$ | 1 | H | H | 4-Cl | H | $CH_3$ | $CH_3$ | |
| 36 | $C_2F_5$ | 1 | H | H | H | H | $CH_2-CH=CH_2$ | $CH_2-CH=CH_2$ | |
| 37 | $CF_3$ | 1 | H | H | H | H | $CH_2-CH=CH_2$ | $CH_2-CH=CH_2$ | |
| 38 | $CF_3$ | 1 | H | H | H | H | $-CH_2-CH_2-$ | | b.p. 89–90°/0.1 mbar |
| 39 | $CF_3$ | 2 | H | H | H | H | $-CH_2-CH_2-$ | | b.p. 92–93°/0.03 mbar |
| 40 | $CF_3$ | 1 | H | H | 4-Cl | H | $-CH_2-CH_2-$ | | b.p. 105–108°/0.1 mbar |
| 41 | $CF_3$ | 1 | H | H | 4-F | H | $-CH_2-CH_2-$ | | b.p. 77–78°/0.02 mbar |
| 42 | $CF_3$ | 2 | H | H | 4-F | H | $-CH_2-CH_2-$ | | b.p. 78–79°/0.15 mbar |
| 43 | $CF_3$ | 1 | H | H | H | H | $-\underset{\underset{CH_3}{\mid}}{CH}-CH_2-$ | | b.p. 77–78°/0.05 mbar |
| 44 | $CF_3$ | 1 | H | H | H | H | $-\underset{\underset{CH_3}{\mid}}{CH}-\underset{\underset{CH_3}{\mid}}{CH}-$ | | b.p. 82–83°/0.07 mbar |
| 45 | $CF_3$ | 1 | H | H | 4-Cl | H | $-\underset{\underset{CH_3}{\mid}}{CH}-CH_2-$ | | |
| 46 | $CClF_2$ | 1 | H | H | 4-$OCH_3$ | H | $-\underset{\underset{C_2H_5}{\mid}}{CH}-CH_2-$ | | |

TABLE 1-continued

| No. | X | n | R₁ | R₂ | R₃ | R₄ | R₅ | R₆ | Physical data (°C.) |
|---|---|---|---|---|---|---|---|---|---|
| 47 | CF₃ | 1 | H | 3-Cl | 4-Cl | H | | —CH₂—CH₂— | |
| 48 | CClF₂ | 1 | H | H | H | H | | —CH₂—CH₂— | |
| 49 | C₂F₅ | 1 | H | H | 4-OCF₃ | H | | —CH₂—CH₂— | |
| 50 | CF₃ | 1 | H | H | 4-OCF₃ | H | | —CH₂—CH₂— | |
| 51 | CF₃ | 1 | H | H | 3-CF₃ | H | | —CH(CH₃)—CH(CH₃)— | |
| 52 | CF₃ | 1 | H | H | 4-OCH₃ | H | | —CH₂—CH₂— | |
| 53 | CF₃ | 1 | H | H | 3-NO₂ | H | | —C(CH₃)₂—C(CH₃)₂— | |
| 54 | CClF₂ | 1 | CH₃ | H | 2-F | H | | —CH₂—CH₂— | |
| 55 | C₂F₅ | 1 | CH₃ | H | 2-F | H | | —CH₂—CH₂— | |
| 56 | CClF₂ | 1 | CH₃ | H | 2-F | H | | —CH(CH₃)—CH(CH₃)— | |
| 57 | CF₃ | 1 | H | 2-Cl | 4-Cl | H | | —CH₂—CH₂— | |
| 58 | CF₃ | 1 | H | 2-Cl | 4-Cl | 5-NO₂ | | —CH₂—CH₂— | |
| 59 | CF₃ | 1 | H | 3-CH₃ | 4-CH₃ | H | | —CH₂—CH₂— | |
| 60 | CClF₂ | 1 | CH₃ | 3-CH₃ | 4-Cl | H | | —CH₂—CH₂— | |
| 61 | CF₃ | 1 | CH₃ | 2-Cl | 4-Cl | 5-CF₃ | | —CH₂—CH₂— | |
| 62 | CF₃ | 1 | H | 2-F | 4-F | 5-NO₂ | | —CH₂—CH₂— | |
| 63 | CF₃ | 1 | H | H | H | H | | —CH₂—CH₂—CH₂— | b.p. 82–83° 0.04 mbar |
| 64 | CF₃ | 2 | H | H | H | H | | —CH₂—CH₂—CH₂— | |
| 65 | CF₃ | 1 | H | H | 4-Cl | H | | —CH₂—CH₂—CH₂— | b.p. 96–98° 0.08 mbar |
| 66 | CF₃ | 1 | H | H | 4-F | H | | —CH₂—CH₂—CH₂— | b.p. 87–89° 0.04 mbar |
| 67 | CF₃ | 1 | H | H | H | H | | —C(CH₃)₂—CH₂—CH(CH₃)— | |
| 68 | C₂F₅ | 1 | H | H | 4-OCF₃ | H | | —CH(CH₃)—CH₂—CH(CH₃)— | |
| 69 | CClF₂ | 1 | H | H | 4-OCH₃ | H | | —CH₂—C(CH₃)₂—CH₂— | |
| 70 | CClF₂ | 1 | H | H | 4-Cl | H | | —CH(C₂H₅)—CH₂—CH₂— | |
| 71 | CF₃ | 1 | CH₃ | H | 3-NO₂ | H | | —CH₂—CH₂—CH₂— | |
| 72 | CF₃ | 1 | CH₃ | H | 3-CF₃ | H | | —CH₂—CH₂—CH₂— | |
| 73 | CF₃ | 1 | CH₃ | 3-Cl | 4-Cl | H | | —CH₂—CH₂—CH₂— | |
| 74 | CF₃ | 1 | H | 3-CH₃ | 4-CH₃ | H | | —C(CH₃)₂—CH₂—C(CH₃)₂— | |
| 75 | C₂F₅ | 1 | H | 3-Cl | 4-Cl | H | | —CH₂—CH₂—CH₂— | |
| 76 | C₃F₇ | 1 | H | H | H | H | | —CH₂—CH₂—CH₂— | |
| 77 | CF₃ | 1 | CH₃ | H | 4-CH₃ | H | | —CH₂—CH₂—CH₂— | |
| 78 | CF₃ | 1 | H | 2-Cl | 4-Cl | 5-NO₂ | | —CH₂—CH₂—CH₂— | |
| 79 | CF₃ | 1 | CH₃ | 2-Cl | 4-Cl | 5-CF₃ | | —CH₂—CH₂—CH₂— | |
| 80 | CClF₂ | 1 | CH₃ | H | H | H | | —CH₂—CH₂—CH₂— | |
| 81 | CF₃ | 2 | CH₃ | H | 4-Cl | H | | —CH₂—C(CH₃)₂—CH₂— | |
| 82 | C₂F₅ | 2 | H | H | 4-CH₃ | H | | —CH₂—CH₂—CH₂— | |
| 83 | CF₃ | 2 | H | 3-Cl | 4-Cl | H | | —CH₂—CH₂—CH₂— | |
| 84 | CF₃ | 1 | CH₃ | 3-NO₂ | 4-Cl | H | | —CH₂—CH₂—CH₂— | |

TABLE 1-continued

| No. | X | n | $R_1$ | $R_2$ | $R_3$ | $R_4$ | $R_5$ | $R_6$ | Physical data (°C.) |
|---|---|---|---|---|---|---|---|---|---|
| 85 | $CF_3$ | 1 | $CH_3$ | H | 3-$NO_2$ | H | | $-CH(C_2H_5)-CH_2-CH_2-$ | |
| 86 | $CF_3$ | 1 | H | H | 2-Cl | H | | $-CH_2-CH_2-CH_2-$ | |
| 87 | $CF_3$ | 1 | H | H | 2-F | H | | $-CH_2-C(CH_3)_2-CH_2-$ | |
| 88 | $CClF_2$ | 1 | H | H | 4-$OCF_3$ | H | | $-CH_2-CH_2-CH_2-$ | |
| 89 | $CF_3$ | 1 | H | H | 4-$SO_2CF_3$ | H | | $-CH_2-CH_2-CH_2$ | |
| 90 | $CF_3$ | 1 | H | H | 4-Cl | H | | $-CH(CH_3)CH_2-CH(CH_3)-$ | b.p. 104-5°/ 0.04 mbar |
| 91 | $CF_3$ | 2 | H | H | 3-$CF_3$ | H | | $-CH_2-CH_2-$ | |
| 92 | $CF_3$ | 1 | H | H | 3-$CF_3$ | H | $CH_3$ | $CH_3$ | |
| 93 | $CF_3$ | 1 | H | H | 3-$CF_3$ | H | $C_2H_5$ | $C_2H_5$ | |
| 94 | $C_2F_5$ | 1 | H | H | H | H | $CH_3$ | $CH_3$ | |
| 95 | $C_2F_5$ | 1 | H | H | H | H | $C_2H_5$ | $C_2H_5$ | |
| 96 | $C_2F_5$ | 1 | H | H | H | H | | $-CH_2-CH_2$ | b.p. 128-130° 0.1 mbar |
| 97 | $C_2F_5$ | 2 | H | H | H | H | | $-CH_2-CH_2$ | |
| 98 | $C_2F_5$ | 1 | H | H | 4-Cl | H | $C_2H_5$ | | |
| 99 | $C_2F_5$ | 1 | H | H | 4-Cl | H | | $-CH_2-CH_2-$ | |
| 100 | $C_2F_5$ | 2 | H | H | 4-Cl | H | | $-CH_2-CH_2-$ | |
| 101 | $C_2F_5$ | 1 | H | H | 4-F | H | $CH_3$ | $CH_3$ | |
| 102 | $C_2F_5$ | 1 | H | H | 4-F | H | $C_2H_5$ | $C_2H_5$ | |
| 103 | $C_2F_5$ | 1 | H | H | 4-F | H | | $-CH_2-CH_2-$ | |
| 104 | $C_2F_5$ | 2 | H | H | 4-F | H | | $-CH_2-CH_2-$ | |
| 105 | $C_2F_5$ | 1 | H | H | 2-F | H | $CH_3$ | $CH_3$ | |
| 106 | $C_2F_5$ | 1 | H | H | 2-F | H | $C_2H_5$ | $C_2H_5$ | |
| 107 | $C_2F_5$ | 1 | H | H | 2-F | H | $-CH_2-CH_2-$ | | |
| 108 | $C_2F_5$ | 2 | H | H | 2-F | H | $-CH_2-CH_2-$ | | |
| 109 | $CF_3$ | 1 | H | H | 2-F | H | $CH_3$ | $CH_3$ | |
| 110 | $CF_3$ | 1 | H | H | 2-F | H | $C_2H_5$ | $C_2H_5$ | |
| 111 | $CF_3$ | 1 | H | H | 2-F | H | | $-CH_2-CH_2-$ | |
| 112 | $CF_3$ | 2 | H | H | 2-F | H | | $-CH_2-CH_2-$ | |
| 113 | $CF_3$ | 1 | H | H | 2-F | H | | $-CH_2-CH_2-CH_2$ | |
| 114 | $CF_3$ | 1 | H | H | 3-$CF_3$ | H | | $-CH(CH_3)-CH_2-$ | b.p. 70-71° 0.08 mbar |
| 115 | $CF_3$ | 1 | H | H | 4-F | H | | $-CH(CH_3)-CH_2-$ | b.p. 80-81° 0.08 mbar |
| 116 | $CF_3$ | 1 | H | H | 3-$CF_3$ | H | | $-CH_2-CH_2-$ | b.p. 70-72° 0.04 mbar |
| 117 | $CF_3$ | 1 | H | 3-$CH_3$ | 4-$CH_3$ | H | | $-CH_2-CH_2-$ | b.p. 92-94° 0.02 mbar |
| 118 | $CF_3$ | 2 | H | H | 4-Cl | H | | $-CH_2-CH_2-$ | b.p. 110-114° 0.04 mbar |
| 119 | $CF_3$ | 1 | H | H | 4-F | H | | $-C_2H_5-C_2H_5$ | b.p. 80-82° 0.4 mbar |
| 120 | $C_2H_5$ | 1 | H | H | H | H | | $-CH(CH_3)-CH_2-$ | b.p. 87-90° 0.13 mbar |
| 121 | $C_2F_5$ | 1 | H | H | H | H | | $-CH(CH_3)-CH_2-$ | b.p. 78-90° 0.15 mbar |
| 122 | $CF_3$ | 1 | H | H | H | H | | $-(CH_3)-CH_2-CH_2-$ | b.p. 91-93° 0.08 mbar |
| 123 | $CF_3$ | 1 | H | H | H | H | | $-CH(CH_3)-CH_2-$ | 0.05 mbar |
| 124 | $CF_3$ | 1 | H | H | 4-Cl | H | | $-CH(CH_3)-CH_2-CH_2-$ | b.p. 97-99° 0.08 mbar |
| 125 | $CF_3$ | 1 | H | H | 4-Cl | H | | $-CH(CH_3)-CH_2-$ | 0.05 mbar |
| 126 | $CF_3$ | 1 | H | H | 3-$CF_3$ | H | | $-CH(CH_3)-CH_2$ | b.p. 80-81° 0.08 mbar |
| 127 | $CF_3$ | 1 | H | H | 4-F | H | | $-CH(CH_3)-CH_2$ | b.p. 82-84° 0.12 mbar |
| 128 | $CF_3$ | 1 | H | H | H | H | | $-CH(C_2H_5)-CH_2-$ | b.p. 80-82 0.03 mbar |
| 129 | $CF_3$ | 1 | H | H | 4-Cl | H | | $-CH(CH_3)-CH(CH_3)-$ | b.p. 97-99° 0.15 mbar |
| 130 | $CF_3$ | 1 | H | H | 3-$CF_3$ | H | | $-CH_2-CH_2-CH_2$ | b.p. 88-90° 0.15 mbar |
| 131 | $CF_3$ | 1 | H | H | H | H | | $-CH_2-CH_2-CH_2-CH_2-$ | b.p. 93-94° 0.09 mbar |
| 132 | $CF_3$ | 1 | H | H | H | H | | $-CH_2CH=CH-CH_2$ | b.p. 92-93° 0.05 mbar |
| 133 | $CF_3$ | 1 | H | H | 2-Cl | H | | $-CH_2-CH_2-$ | b.p. 91-92° 0.09 mbar |
| 134 | $CF_3$ | 1 | H | H | 4-$CH_3$ | H | | $-CH_2-CH_2-$ | b.p. 82-83° 0.04 mbar |

TABLE 1-continued

| No. | X | n | R1 | R2 | R3 | R4 | R5 | R6 | Physical data (°C.) |
|---|---|---|---|---|---|---|---|---|---|
| 135 | CF3 | 1 | H | H | 4-Cl | H | | —CH2CH=CH—CH2— | b.p. 107–109° 0.08 mbar |
| 136 | CF3 | 1 | H | H | 4-Cl | H | | —CH2—C(CH3)2—CH2— | b.p. 104–106° 0.09 mbar |
| 137 | CF3 | 1 | H | H | 4-CH3 | H | | —CH2—C(CH3)2—CH2— | |
| 138 | CF3 | 1 | H | H | 2-Cl | H | | —CH2—C(CH3)2—CH2 | |
| 139 | CF3 | 1 | H | H | 4-CH3 | H | | —CH(CH2)—CH2— | |
| 140 | CF3 | 1 | H | H | 4-CH3 | H | | —CH2—CH2—CH2— | |
| 141 | CF3 | 1 | H | H | 4-CH3 | H | CH3 | CH3 | |
| 142 | CF3 | 1 | H | H | 4-CH3 | H | C2H5 | C2H5 | |
| 143 | CF3 | 2 | H | H | 4-CH3 | H | | —CH2—CH2— | |
| 144 | CF3 | 2 | H | H | 2-Cl | H | | —CH2—CH2— | |
| 145 | CF3 | 2 | H | H | 4-CH3 | H | | —CH2—CH2—CH2— | |
| 146 | CF3 | 2 | H | H | 4-Cl | H | | —CH2—CH2—CH2— | |
| 147 | CF3 | 2 | H | H | H | H | | —CH2—CH2—CH2— | |
| 148 | CF3 | 2 | H | H | 2-Cl | H | | —CH2—CH2—CH2— | |
| 149 | CF3 | 2 | H | H | 3-CH3 | H | | —CH2—CH2—CH2— | |
| 150 | CF3 | 2 | H | H | 3-CH3 | H | | —CH2—CH2—CH2— | |
| 151 | CF2 | 2 | H | H | H | H | | —CH2—CH2— | |

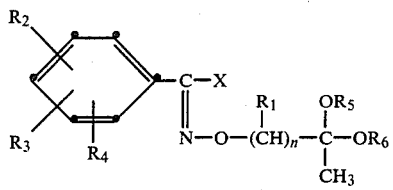

| 161 | CF3 | 1 | H | H | H | H | | —CH2—CH2 |
| 162 | CF3 | 1 | H | H | 4-Cl | H | | —CH2—CH2— |

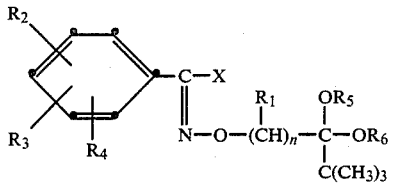

| 171 | | 1 | H | H | H | H | | —CH2—CH2 |
| 172 | | 1 | H | H | 4-Cl | H | | —CH2—CH2 |

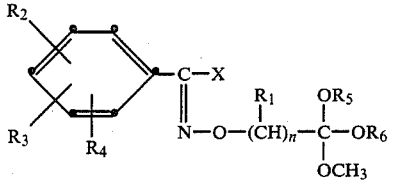

| 181 | CF3 | 1 | H | H | H | H | CH3 | CH3 |
| 182 | CF3 | 1 | H | H | H | H | C2H5 | C2H5 |
| 183 | CF3 | 1 | H | H | H | H | | —CH2—CH2— |
| 184 | CF3 | 1 | H | H | 4-Cl | H | | —CH2—CH2— |
| 185 | CF3 | 1 | H | H | 4-Cl | H | C2H5 | C2H5 |

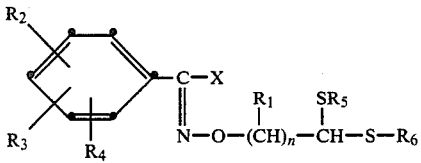

| 186 | CF3 | 1 | H | H | H | H | | —CH2—CH |
| 187 | CF3 | 1 | H | H | 4-Cl | H | | —CH2—CH2 |
| 188 | CF3 | 1 | H | H | 4-CH3 | H | | —CH2—CH2 |
| 189 | CF3 | 1 | H | H | 4-F | H | | —CH2—CH2— |
| 190 | CF3 | 1 | H | H | H | H | | —CH2—CH2—CH2— |
| 191 | CF3 | 1 | H | H | 4-Cl | H | | —CH2—CH2—CH2— |

TABLE 1-continued

| No. | X | n | $R_1$ | $R_2$ | $R_3$ | $R_4$ | $R_5$ | $R_6$ | Physical data (°C.) |
|---|---|---|---|---|---|---|---|---|---|

Structure:
$$\begin{array}{c}R_2\\ \diagup\\ \phantom{x}\phantom{x}\phantom{x}-C-X\\ R_3\phantom{xx}R_4\phantom{xxx}\|\phantom{xxx}R_1\phantom{xxx}SR_5\\ \phantom{xxxxxxxx}N-O-(CH)_n-C-SR_6\\ \phantom{xxxxxxxxxxxxxxxxxx}CH_3\end{array}$$

| No. | X | n | $R_1$ | $R_2$ | $R_3$ | $R_4$ | $R_5$ | $R_6$ | Physical data (°C.) |
|---|---|---|---|---|---|---|---|---|---|
| 192 | CF$_3$ | 1 | H | H | H | H | | —CH$_2$—CH$_2$— | |
| 193 | CF$_3$ | 1 | H | H | 4-Cl | H | | —CH$_2$—CH$_2$ | |
| 194 | CF$_3$ | 1 | H | H | 4-CH$_3$ | H | | —CH$_2$—CH$_2$ | |
| 195 | CF$_3$ | 1 | H | H | 4-F | H | | —CH$_2$—CH$_2$— | |
| 196 | CF$_3$ | 1 | H | H | H | H | | —CH$_2$—CH$_2$—CH$_2$— | |
| 197 | CF$_3$ | 1 | H | H | 4-Cl | H | | —CH$_2$—CH$_2$—CH$_2$— | |

Structure:
$$\begin{array}{c}R_2\\ \diagup\\ \phantom{x}\phantom{x}\phantom{x}-C-X\\ R_3\phantom{xx}R_4\phantom{xxx}\|\phantom{xxx}R_1\phantom{xxx}SR_6\\ \phantom{xxxxxxxx}N-O-(CH)_n-C-SR_6\\ \phantom{xxxxxxxxxxxxxxxxxx}OCH_3\end{array}$$

| No. | X | n | $R_1$ | $R_2$ | $R_3$ | $R_4$ | $R_5$ | $R_6$ | Physical data (°C.) |
|---|---|---|---|---|---|---|---|---|---|
| 201 | CF$_3$ | 1 | H | H | H | H | | —CH$_2$—CH$_2$— | |
| 202 | CF$_3$ | 1 | H | H | 4-Cl | H | | —CH$_2$—CH$_2$— | |
| 203 | CF$_3$ | 1 | H | H | 4-CH$_3$ | H | | —CH$_2$—CH$_2$— | |
| 204 | CF$_3$ | 1 | H | H | 4-F | H | | —CH$_2$—CH$_2$— | |

Structure:
$$\begin{array}{c}R_2\\ \diagup\\ \phantom{x}\phantom{x}\phantom{x}-C-X\\ R_3\phantom{xx}R_4\phantom{xxx}\|\phantom{xxx}R_1\phantom{xxx}OR_5\\ \phantom{xxxxxxxx}N-O-(CH)_n-CH\phantom{xxx}R_6\\ \phantom{xxxxxxxxxxxxxxxxxx}CH_2\end{array}$$

| No. | X | n | $R_1$ | $R_2$ | $R_3$ | $R_4$ | $R_5$ | $R_6$ | Physical data (°C.) |
|---|---|---|---|---|---|---|---|---|---|
| 211 | CF$_3$ | 1 | H | H | H | H | | 2-furanyl | |
| 212 | CF$_3$ | 1 | H | H | 4-Cl | H | | 2-furanyl | b.p. 89–99° C./ 0.07 mbar |
| 213 | CF$_3$ | 1 | H | H | 4-F | H | | 2-furanyl | |
| 214 | CF$_3$ | 1 | H | H | 4-CH$_3$ | H | | 2-furanyl | |
| 215 | CF$_3$ | 1 | H | H | 2-Cl | H | | 2-furanyl | |
| 216 | CF$_3$ | 1 | H | H | 3-CH$_3$ | 4-CH$_3$ | | 2-furanyl | |
| 217 | CF$_3$ | 1 | H | H | H | 3-CF$_3$ | | 2-furanyl | |
| 218 | CF$_3$ | 1 | H | H | H | H | | 2-furanyl | |
| 219 | CF$_3$ | 1 | H | H | H | H | | 2-pyranyl | |
| 220 | CF$_3$ | 1 | H | H | 4-Cl | H | | 2-pyranyl | |
| 221 | CF$_3$ | 1 | H | H | 4-CH$_3$ | H | | 2-pyranyl | |

EXAMPLE 5

Formulation examples for compounds of formula I or mixtures thereof with herbicides (percentages are by weight)

| (a) Wettable powders | (a) | (b) | (c) |
|---|---|---|---|
| Compound of formula I or mixtures thereof with a herbicide | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| Compound of formula I or mixture thereof with a herbicide | 10% | 1% |
| octylphenol polyethylene glycol ether (4–5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I or mixture thereof with a herbicide | 0.1% | 1% |

-continued

| (c) Dusts | (a) | (b) |
|---|---|---|
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I or mixture thereof with a herbicide | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I or mixture thereof with a herbicide | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I or mixture thereof with a herbicide | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I or mixture thereof with a herbicide | 5% |
| isopropylamine | 1% |
| octylphenol polyethylene glycol ether (78 moles of ethylene oxide) | 3% |
| water | 91% |

Biological Examples

The ability of the compounds of formula I to protect cultivated plants from the phytotoxic effects of potent herbicides is illustrated in the following Examples. In the test procedures the compounds of formula I are referred to as antidotes.

EXAMPLE 6

Test with antidote and herbicide in maize.
Preemergence ppi application of antidote and herbicide as tank mixture The compound for testing as safener is sprayed onto the soil together with the herbicide and the mixture is then incorporated into the soil. Plastic containers measuring 25 cm×17 cm×10 cm are then filled with the treated soil and LG 5 maize seeds are sown therein. The protective action of the safener is then evaluated (in %) 21 days after application. The plants treated with herbicide alone and the completely untreated plants are used for reference purposes. A good (significant) safener effect is achieved if the phytoxicity of severe to average plant damage can be reduced to slight, reversible damage or to complete tolerance. A protective action of at least 25% is normally sufficient for this. The results are reported below.

Herbicide: S-ethyl dipropylthiocarbamate "EPTC".
Antidote: 1-(4-chlorphenyl)-1-(3,5-dioxolan-2-ylmethoximino)-2,2,2-trifluoroethane (compound 40).

| | Herbicide | antidote | Protective action in % |
|---|---|---|---|
| Rate of application in kg/Hectare | 8 | — | 0 |
| | 8 | 8 | 38 |
| | 8 | 4 | 50 |
| | 8 | 2 | 75 |
| | 4 | — | 0 |
| | 4 | 4 | 50 |
| | 4 | 2 | 75 |
| | 4 | 1 | 75 |

EXAMPLE 7

Preemergence test with antidote and herbicide in sorghum. Application of the antidote by seed dressing Funk G 522 sorghum seeds are mixed with the compound for testing as safener in a glass beaker. Seeds and compound are thoroughly mixed by shaking and rotating the beaker. Then plastic containers measuring 25 cm×17 cm×12 cm are filled with sandy loam and the dressed seeds are sown therein. The seeds are covered and the herbicide is then sprayed onto the surface of the soil. The protective action of the safener is evaluated (in %) 19 days after application. The plants treated with herbicide alone and the completely untreated controls are used for reference purposes. The results are reported below.

Herbicide: N-chloroacetyl-N-(2-methoxy-1-methylethyl)-2-ethyl-6-methylaniline ("metolachlor").
Antidote: 1-(4-chlorophenyl)-1-(3,5-dioxolan-2-ylmethoximino)-2,2,2-trifluoroethane (compound 40).

| Rate of application in kg/hectare | | Protective action |
|---|---|---|
| Herbicide | antidote | in % |
| 4 | 0 | 0 |
| 4 | 1 | 38 |
| 4 | 0.5 | 63 |
| 4 | 0.25 | 63 |
| 2 | 0 | 0 |
| 2 | 1 | 38 |
| 2 | 0.5 | 63 |
| 2 | 0.25 | 63 |
| 2 | 0.125 | 63 |
| 1 | 0 | 0 |
| 1 | 1 | 50 |
| 1 | 0.5 | 63 |

-continued

| Rate of application in kg/hectare | | Protective action |
|---|---|---|
| Herbicide | antidote | in % |
| 1 | 0.25 | 75 |
| 1 | 0.125 | 88 |

Other tests result in the following values:

| Rate of application in kg/hectare | | Protective action |
|---|---|---|
| Herbicide | antidote | in % |
| 4 | 0 | 0 |
| 4 | 2 | 50 |
| 4 | 1 | 63 |
| 4 | 0.5 | 63 |
| 2 | 0 | 0 |
| 2 | 2 | 50 |
| 2 | 1 | 63 |
| 2 | 0.5 | 63 |
| 1 | 0 | 0 |
| 1 | 2 | 50 |
| 1 | 1 | 63 |
| 1 | 0.5 | 63 |
| 2 | 0 | 0 |
| 4 | 4 | 50 |
| 4 | 2 | 63 |
| 4 | 1 | 63 |
| 2 | 0 | 0 |
| 2 | 4 | 50 |
| 2 | 2 | 50 |
| 2 | 1 | 50 |
| 2 | 0.5 | 50 |
| 1 | 0 | 0 |
| 1 | 4 | 25 |
| 1 | 2 | 25 |
| 1 | 1 | 38 |
| 1 | 0.5 | 50 |

In a further test, N-chloroacetyl-N-methoxymethyl-2,6-diethylaniline ("alachlor") is used as herbicide and 1-(4-chlorophenyl)-1-(1,3-dioxolan-2-ylmethoximino)-2,2,2-trifluoroethane (compound 40) as antidote.

| Rate of application in kg/hectare | | Protective action |
|---|---|---|
| Herbicide | antidote | in % |
| 4 | 0 | 0 |
| 4 | 2 | 63 |
| 4 | 1 | 75 |
| 2 | 0 | 0 |
| 2 | 4 | 50 |
| 2 | 2 | 63 |
| 2 | 1 | 75 |
| 2 | 0.5 | 75 |
| 1 | 0 | 0 |
| 1 | 4 | 38 |
| 1 | 2 | 50 |
| 1 | 1 | 63 |
| 1 | 0.5 | 63 |

EXAMPLE 8

Test with antidote and herbicide in sorghum.
Preemergence application of herbicide and antidote as tank mixture Plastic containers measuring 25 cm × 17 cm × 12 cm are filled with sandy loam and Funk G 522 sorghum seeds are sown therein. The seeds are covered and the compound for testing as safener is then sprayed, together with the herbicide, in dilute solution as tank mixture onto the surface of the soil. The protective action of the safener is evaluated (in %) 30 days after application. The plants treated with herbicide alone and the completely untreated controls are used for reference purposes. The results are reported below.

Herbicide: N-chloroacetyl-N-(2-methoxy-1-methyl)-2-ethyl-6-methylaniline ("metolachlor").

Antidote: 1-(4-chlorophenyl)-1-(1,3-dioxolan-2-ylmethoximino)-2,2,2-trifluoroethane (compound 40).

| Rate of application in kg/hectare | | | | | | | | | |
|---|---|---|---|---|---|---|---|---|---|
| Herbicide + antidote | 4 0 | 4 4 | 4 2 | 2 0 | 2 2 | 2 1 | 1 0 | 1 1 | 1 0.5 |
| Protective action in % | 0 | 63 | 63 | 0 | 63 | 63 | 0 | 50 | 50 |

In a further test, N-chloroacetyl-N-methoxymethyl-2,6-diethylaniline is used as herbicide and 1-(4-chlorophenyl)-1-(1,3-dioxolan-2-ylmethoximino)-2,2,2-trifluoroethane as antidote. The test is carried out with Funk G 522 sorghum seed without the addition of weeds.

| Rate of application in kg/hectare | | Protective action |
|---|---|---|
| Herbicide | antidote | in % |
| 2 | 0 | 0 |
| 2 | 2 | 75 |
| 2 | 1 | 88 |
| 1 | 0 | 0 |
| 1 | 1 | 75 |
| 1 | 0.5 | 75 |

EXAMPLE 9

Test with antidote and herbicide in soybeans.
Preemergence application of herbicide and antidote as tank mixture Pots (diameter at the top 6 cm) are filled with sandy loam and "Hark" soybean seeds are sown therein. The seeds are covered and the compound for testing as safener, together with the herbicide, is sprayed in dilute solution as tank mixture onto the surface of the soil. The protective action is evaluated (in %) 21 days after application. The plants treated with herbicide alone and the completely untreated controls are used for reference purposes. The results are reported below.

Herbicide: 4-amino-6-tert-butyl-4,5-dihydro-3-methylthio-1,2,4-triazin-5-one ("metribuzin").

| Rate of application | | |
|---|---|---|
| antidote | Herbicide | Relative protective action |
| No. 1 1.5 kg/ha | 0.75 kg/ha | 25% |
| No. 2 1.5 kg/ha | 0.75 kg/ha | 25% |
| No. 11 1.5 kg/ha | 0.75 kg/ha | 25% |

EXAMPLE 10

Test with antidote and herbicide in wheat.
Postemergence application of herbicide and antidote as tank mixture "Farnese" wheat seeds are sown in plastic pots (diameter at the top 11 cm) containing 0.5 liter of earth in a greenhouse. The seeds are covered and the compound for testing as safener is applied postemergence, together with the herbicide, as tank mixture. The protective action of the safener is evaluated (in %) 20 days after application. The plants treated with herbicide alone and the completely untreated controls are used for reference purposes. The results are reported below:

Herbicide: Propargyl α-[4-(2,4-dichloropyridyl-2-oxy)phenoxy]-propionate.

| Rate of application | | Relative protective action |
|---|---|---|
| antidote | Herbicide | |
| No. 2 1.5 kg/ha | 0.75 kg/ha | 25% |
| No. 40 1.5 kg/ha | 0.75 kg/ha | 25% |
| No. 41 1.5 kg/ha | 0.75 kg/ha | 25% |
| No. 65 1.5 kg/ha | 0.75 kg/ha | 50% |

EXAMPLE 11

Test with antidote and herbicide in rice. Application of the antidote during immersion of the rice seeds, and preemergence application of the herbicide to the moist soil Rice seeds are immersed for 48 hours in 100 ppm solutions of the compound for testing as safener. The seeds are then allowed to dry for about 2 hours until they are no longer tacky. Plastic containers measuring 25 cm×17 cm×12 cm are filled with sandy loam to 2 cm below the edge. The pretreated seeds are sown on the surface of the soil in the containers and only lightly covered. The soil is kept in a moist (non-marshy) state. Then a dilute solution of the herbicide is sprayed onto the surface of the soil. The water level is then gradually raised in accordance with growth of the rice plants. The protective action of the safener is evaluated (in %) 18 days after application. The plants treated with herbicide alone and the completely untreated controls are used for reference purposes. The results are as follows:

Herbicide: 2-chloro-2',6'-diethyl-N-(2''-propoxyethyl)acetamide ("pretilachlor").

| Rate of application | | Relative protective action |
|---|---|---|
| antidote | Herbicide | |
| No. 63 100 ppm | 0.25 kg/ha | 25% |

EXAMPLE 12

Test with antidote and herbicide in rice. Application of the antidote as seed dressing and preemergence application of the herbicide to the moist soil Rice seeds are mixed with the compound for testing as safener in a glass beaker. Seeds and compound are thoroughly mixed by shaking and rotating. Containers measuring 47 cm×29 cm×24 cm are then filled with sandy loam and the dressed seeds are sown therein. The seeds are covered and the herbicide is then sprayed in dilute solution onto the surface of the soil. About 20 days after sowing when the rice plants are in the 3-leaf stage, the surface of the soil is covered with water to a height of 4 cm. The protective action of the safener is evaluated (in %) 30 days after the application of the herbicide. The plants treated with herbicide alone and the completely untreated controls are used for reference purposes. The results are as follows:

Herbicide: 2,6-dinitro-N,N-dipropyl-4-trifluoromethylaniline ("trifluralin").

| Rate of application | | Relative protective action |
|---|---|---|
| antidote | Herbicide | |
| No. 40 2 g/kg of seeds | 2 kg/ha | 25% |
| No. 40 2 g/kg of seeds | 1 kg/ha | 38% |

Herbicide: Methyl-α-[4-(2,4-dichlorophenoxy)-phenoyx]propionate ("hoelon").

| Rate of application | | Relative protective action |
|---|---|---|
| antidote | Herbicide | |
| No. 40 1 g/kg of seeds | 1 kg/ha | 50% |
| No. 40 2 g/kg of seeds | 0.5 kg/ha | 63% |
| No. 40 1 g/kg of seeds | 1 kg/ha | 25% |
| No. 40 1 g/kg of seeds | 0.5 kg/ha | 38% |

Herbicide: Propargyl α-[4-(2',4'-dichloropyridyl-2'-oxy)phenoxy]propionate.

| Rate of application | | Relative protective action |
|---|---|---|
| antidote | Herbicide | |
| No. 40 2 g/kg of seeds | 0.5 kg/ha | 50% |
| No. 40 2 g/kg of seeds | 0.25 kg/ha | |

What is claimed is:

1. An oxime ether of the formula $$\begin{array}{c} R_2 \\ \\ R_3 \end{array} \underset{R_4}{\overset{}{\bigotimes}} \begin{array}{c} \underset{\parallel}{C}-X \\ N-O-(CH)_n \end{array} \underset{\underset{\text{}}{\mid}}{\overset{R_1}{\underset{\text{}}{\mid}}} \underset{\underset{\text{}}{\mid}}{\overset{Y}{\underset{\text{}}{\mid}}} \underset{OR_6}{\overset{OR_5}{\diagup}}$$

wherein
n is 1 or 2;
each of $R_1$ and $R_2$ is hydrogen or $C_1$–$C_4$-alkyl;
each of $R_3$ and $R_4$ is hydrogen, halogen, $C_1$–$C_4$ alkyl, $C_1$–$C_4$ haloalkyl, $C_1$–$C_4$ alkoxy, $C_1$–$C_4$ haloalkoxy or nitro;
$R_5$ and $R_6$ together form a 3 to 4-membered alkylene or alkenylene bridge which unsubstituted or substituted by 1 or 2 $C_1$–$C_4$ alkyl groups;
X is fluorinated $C_1$–$C_3$ alkyl radical which may also additionally contain chlorine; and
Y is hydrogen, $C_1$–$C_4$ alkyl or $C_1$–$C_4$ alkoxy.

2. An oxime ether of claim 1 wherein n is 1 or 2, $R_1$ and $R_2$ are hydrogen, $R_3$ and $R_4$ are hydrogen, halogen, $C_1$–$C_4$ alkyl or $C_1$–$C_4$ haloalkyl, $R_5$ and $R_6$ together form a 3- to 4-membered alkylene or alkenylene bridge which is unsubstituted or substituted by 1 or 2 $C_1$–$C_4$ alkyl groups, X is a trifluoromethyl and Y is hydrogen.

3. 1-Phenyl-1-(1,3-dioxan-2-yl-methoximino)-2,2,2-trifluoroethane of claim 1.

4. 1-(4-Chlorophenyl)-1-(1,3-dioxan-2-yl-methoximino)-2,2,2-trifluoroethane of claim 1.

5. 1-(4-Flurophenyl)-1-(1,3-dioxan-2-yl)-methoximino-2,2,2-trifluoroethane of claim 1.

6. A composition for controlling weeds in crops of culture plants which comprises (a) a herbicidally effective amount of a herbicide selected from the group consisting of thiocarbamates, haloacetanilides, phenoxyphenoxypropionates, pyridyloxyphenoxypropionates and dinitroanilines, and (b) as crop safening agent an oxime ether of the formula

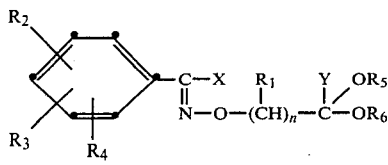

wherein
n is 1 or 2;
each of $R_1$ and $R_2$ is hydrogen or $C_1$-$C_4$-alkyl;
each of $R_3$ and $R_4$ is hydrogen, halogen, $C_1$-$C_4$ alkyl, $C_1$-$C_4$ haloalkyl, $C_1$-$C_4$ alkoxy, $C_1$-$C_4$ haloalkoxy or nitro;
$R_5$ and $R_6$ together form a 3 to 4-membered alkylene or alkenylene bridge which is unsubsituted or substituted by 1 or 2 $C_1$-$C_4$ alkyl groups;
X is fluorinated $C_1$-$C_3$ alkyl radical which may also additionally contain chlorine; and
Y is hydrogen, $C_1$-$C_4$ alkyl or $C_1$-$C_4$ alkoxy.

7. A composition of claim 6 in which the herbicide is a haloacetanilide of the formula

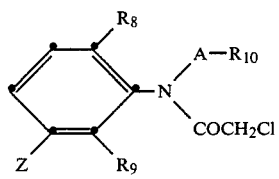

wherein
each of $R_8$ and $R_9$ is hydrogen, halogen, lower alkyl or lower alkoxy, Z is hydrogen or lower alkyl,
A is methylene, 1-1-ethylene or 1,2-ethylene, each of which is unsubstituted or substituted by 1 or 2 lower alkyl groups, and $R_{10}$ is lower alkoxy, allyloxy, lower alkoxycarbonyl, N,N-di(lower alkyl)-carbamoyl, N-propargylcarbamoyl, cyano, ethynyl, 1,3-dioxolan-2-yl, 2-tetrahydrofuranyl, unsubstituted or substituted benzoyl, unsubstituted or substituted 1,3,4-oxadiazol-2-yl or unsubstituted or substituted 1,3,4-triazol-2-yl.

8. A method of protecting rice, sorghum, wheat and maize crops from the phytoxic action of thiocarbamate, triazinone haloacetanilide, phenoxyphenoxypropionate, pyridyloxyphenoxypropionate or dinitroaniline herbicides, which comprises adding to the herbicides, applying to the locus of the crops, or applying to the seeds of said crops, as antidote, a compound of the formula

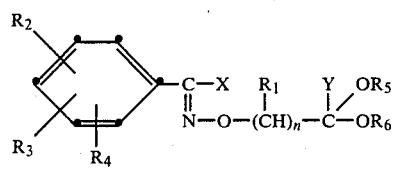

wherein
n is 1 or 2;
each of $R_1$ and $R_2$ is hydrogen or $C_1$-$C_4$-alkyl;
each of $R_3$ and $R_4$ is hydrogen, halogen, $C_1$-$C_4$ alkyl, $C_1$-$C_4$ haloalkyl, $C_1$-$C_4$ alkoxy, $C_1$-$C_4$ haloalkoxy or nitro;
$R_5$ and $R_6$ together form a 3 to 4-membered alkylene or alkenylene bridge which is unsubstituted or substituted by 1 or 2 $C_1$-$C_4$ alkyl groups;
X is fluorinated $C_1$-$C_3$ alkyl radical which may also additionally contain chlorine; and
Y is hydrogen, $C_1$-$C_4$ alkyl or $C_1$-$C_4$ alkoxy.

9. A method of claim 8 in which the compound is 1-phenyl-1-(1,3-dioxan-2-yl-methoximino)-2,2,2-trifluoroethane.

10. A method of claim 8 in which the compound is 1-(4-chlorophenyl)-1-(1,3-dioxan-2-yl-methoximino)-2,2,2-trifluoroethane.

11. A method of claim 8 in which the herbicide is propargyl[4-(2,4-dichloropyridyl-2-oxy)-phenoxy]-propionate.

12. A method of claim 8 in which the herbicide is 2-chloro-2',6'-diethyl-N-(2''-propoxyethyl) acetamide.

* * * * *